US012630532B2

(12) United States Patent
Liu et al.

(10) Patent No.: US 12,630,532 B2
(45) Date of Patent: May 19, 2026

(54) INDOLE-SUBSTITUTED QUINOLINES AND THEIR COMBINATION WITH PLK1 INHIBITORS FOR THE TREATMENT OF CANCER

(71) Applicant: UNIVERSITY OF KENTUCKY RESEARCH FOUNDATION, Lexington, KY (US)

(72) Inventors: Chunming Liu, Lexington, KY (US); David S Watt, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 377 days.

(21) Appl. No.: 18/567,275

(22) PCT Filed: Jun. 21, 2022

(86) PCT No.: PCT/US2022/034309

§ 371 (c)(1),
(2) Date: Dec. 5, 2023

(87) PCT Pub. No.: WO2022/271676

PCT Pub. Date: Dec. 29, 2022

(65) Prior Publication Data

US 2024/0300921 A1 Sep. 12, 2024

Related U.S. Application Data

(60) Provisional application No. 63/213,584, filed on Jun. 22, 2021.

(51) Int. Cl.

| | |
|---|---|
| ***C07D 401/14*** | (2006.01) |
| ***A61K 31/4709*** | (2006.01) |
| ***A61K 31/496*** | (2006.01) |
| ***A61K 45/06*** | (2006.01) |
| ***A61P 35/00*** | (2006.01) |
| ***C07D 401/04*** | (2006.01) |

(52) U.S. Cl.

CPC ........ *C07D 401/14* (2013.01); *A61K 31/4709* (2013.01); *A61K 31/496* (2013.01); *A61K 45/06* (2013.01); *A61P 35/00* (2018.01); *C07D 401/04* (2013.01)

(58) Field of Classification Search

CPC ..... C07D 401/14; C07D 401/04; A61P 35/00; A61K 31/4709; A61K 31/496; A61K 45/06

See application file for complete search history.

(56) References Cited

U.S. PATENT DOCUMENTS

2016/0280654 A1 9/2016 Akbarali et al.

OTHER PUBLICATIONS

Ortiz et al., 11(12) PLoS Negl. Trop. Dis.: e0006157 (2017) (Year: 2017).*

Pubchem-SID:394725341 Deposit Date: Dec. 6, 2019 (Dec. 6, 2019) pp. 1-5.

Pubchem-SID:440644970 Deposit Date: Feb. 22, 2021 (Feb. 22, 2021) pp. 1-5.

Hoemann et al. 'Potent In Vitro Methicillin-Resistant *Staphylococcus aureus* Activity of 2-(1HIndo1-3-yl)quinoline Derivatives', Bioorganic & Medicinal Chemistry Letters, 2000, vol. 10, pp. 2675-2678.

* cited by examiner

*Primary Examiner* — Timothy R Rozof

(74) *Attorney, Agent, or Firm* — Stites & Harbison PLLC; Patrick M. Torre

(57) ABSTRACT

Indole-substituted quinolines (ISQs) are provided which may include a variety of substituted piperidines. Methods for treating cancers, including c-MYC-driven cancers, are described including administering the ISQs to a subject in need thereof. The compounds may be administered in combination with a polo-like kinase-1 (Plk1) inhibitor. The Plk1 and the compound may be administered in synergistically effective amounts.

28 Claims, 18 Drawing Sheets

ISQ-1

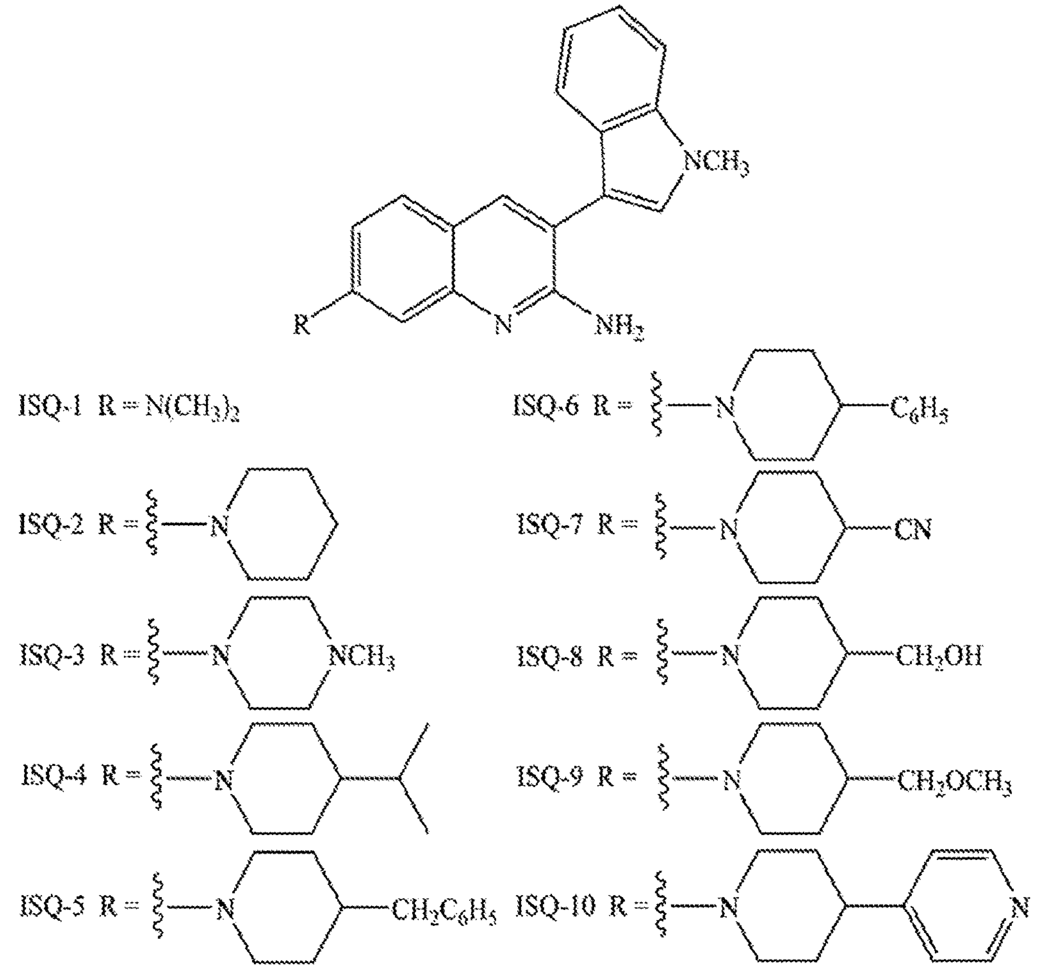

ISQ-1 R = $N(CH_3)_2$

ISQ-2 R =

ISQ-3 R =

ISQ-4 R =

ISQ-5 R =

ISQ-6 R =

ISQ-7 R =

ISQ-8 R =

ISQ-9 R =

ISQ-10 R =

FIG. 2A

| R | ISQ code | 62 nM | 125 nM | 250 nM | 500 nM |
|---|---|---|---|---|---|
| N,N-dimethylamino | ISQ-1 | 16 ± 2 | 22 ± 5 | 38 ± 2.2 | 91 ± 4.3 |
| N-piperidinyl | ISQ-2 | 8.2 ± 5.6 | 28 ± 4.6 | 55 ± 0.5 | 97 ± 0.4 |
| 4-N-methylpiperazinyl | ISQ-3 | ND | ND | 27 ± 14 | 89 ± 2.1 |
| 4-N-(isopropyl)piperazinyl | ISQ-4 | ND | ND | ND | 36 ± 0.9 |
| 4-N-benzylpiperazinyl | ISQ-5 | ND | ND | ND | 21 ± 3.9 |
| 4-N-phenylpiperazinyl | ISQ-6 | ND | ND | ND | 56 ± 13 |
| 4-N-cyanopiperazinyl | ISQ-7 | 19 ± 5.5 | 89 ± 0.2 | 98 ± 0.6 | 97 ± 0.7 |
| 4-N-(hydroxylmethyl)piperazinyl | ISQ-8 | 20 ± 9 | 59 ± 2.7 | 97 ± 0.2 | 98 ± 0.6 |
| 4-N-(methoxylmethyl)piperazinyl | ISQ-9 | 12 ± 1.9 | 55 ± 2.3 | 98 ± 0 | 99 ± 0.1 |
| 4-N-(4-pyridyl)piperazinyl | ISQ-10 | 21 ± 5.7 | 84 ± 2.7 | 99 ± 0.2 | 99 ± 0.1 |

FIG. 2B

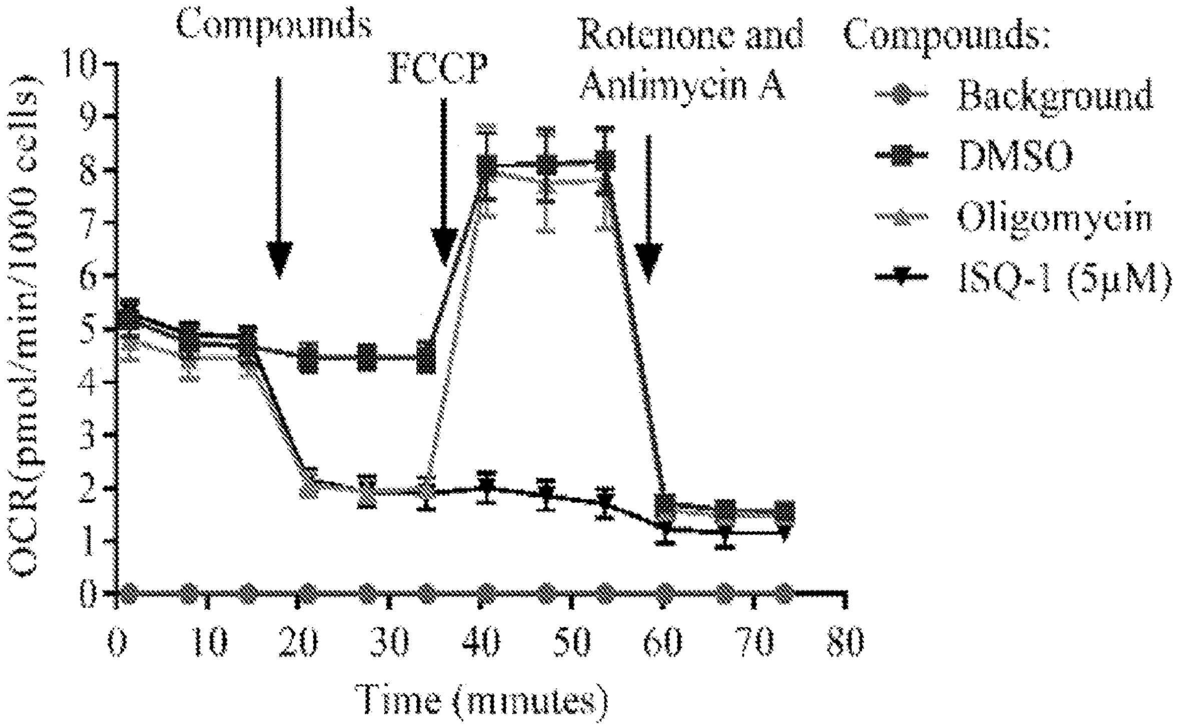
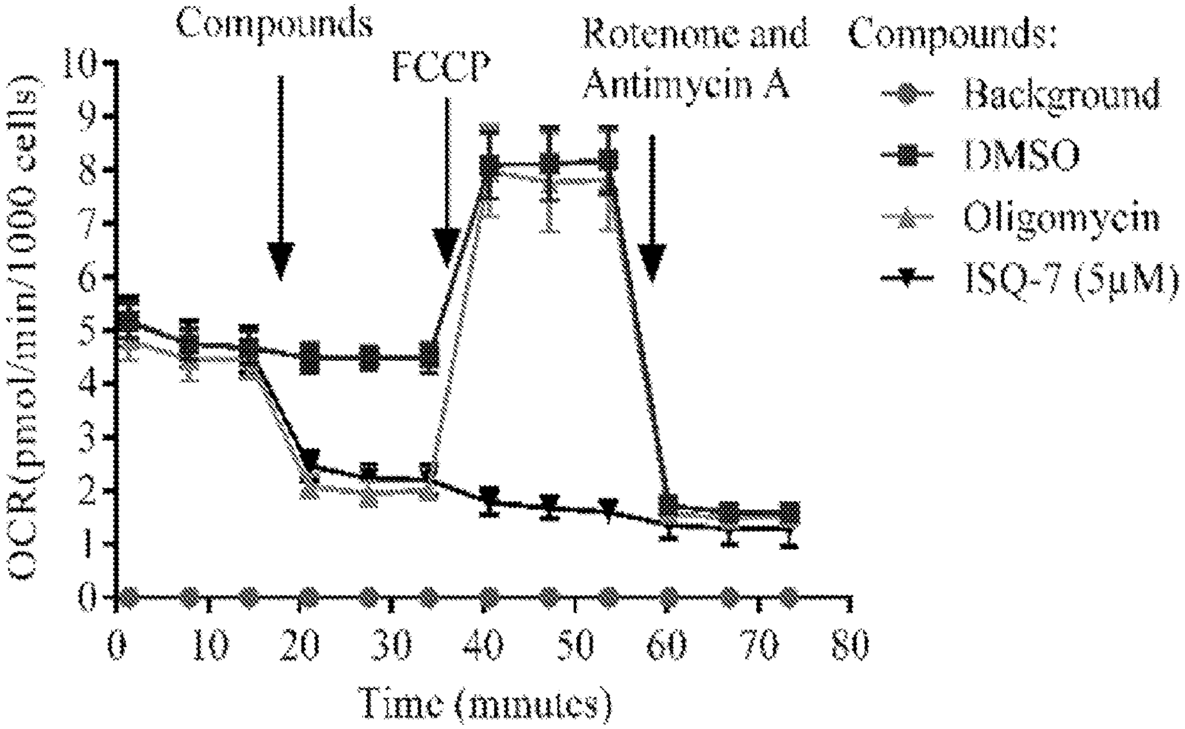
FIG. 10

INDOLE-SUBSTITUTED QUINOLINES AND THEIR COMBINATION WITH PLK1 INHIBITORS FOR THE TREATMENT OF CANCER

RELATED APPLICATIONS

This application is a national phase utility patent application claiming the benefit of priority in international application no. PCT/US2022/34309 filed Jun. 21, 2022, which in turn claims priority to U.S. Provisional Application Ser. No. 63/213,584 filed Jun. 22, 2021, the entire disclosures of each of which are incorporated herein by reference.

GOVERNMENT INTEREST

This invention was made with government support under grant numbers CA172379 and CA177558 awarded by the National Cancer Institute (NCI). The government has certain rights in the invention.

TECHNICAL FIELD

The present invention relates to compounds for the treatment of cancer. In particular, the presently-disclosed subject matter relates to indole-substituted quinolones and their combination with Plk1 inhibitors and methods of use thereof for the treatment of cancer.

BACKGROUND

Metabolic reprograming in tumors generates anabolic intermediates for the biosynthesis of lipids, carbohydrates, and nucleic acids that are necessary to promote tumor growth, and this reprogramming includes the well-known Warburg effect in which cancer cells up-regulate glycolysis. This glycolytic up-regulation is not, however, a consequence of the down-regulation of oxidative phosphorylation in cancer cells (1) that maintain their capacity to produce ATP through mitochondrial, oxidative phosphorylation (2-4). In fact, emerging evidence suggests that activation of oncogenes and inactivation of tumor suppressors promote mitochondrial biogenesis that drives tumorigenesis and maintains viable populations of cancer stem cells (5). Additional studies point to the up-regulation of genes in the oxidative phosphorylation pathway as an important part of the resistance mechanisms against therapeutic, antineoplastic agents (6-8). In a study that compared sixteen normal cell lines and thirty-one cancer cell lines, the average percentage contribution of oxidative phosphorylation to ATP production was well-matched: 83% for cancer cells and 80% for normal cells (9). In addition, 63% of rectal adenocarcinomas and 53% of colon adenocarcinomas harbor tumor-specific, non-synonymous mutations in mitochondrial DNA (mtDNA) that encodes protein subunits of electron transport complexes I to V (10,11). Cancer cell lines with mtDNA-encoded mutations in complex I subunits were up to twenty-fold more sensitive to complex I inhibitors, such as metformin and phenformin, than the sensitivity of non-mutated complex I in normal cell lines (12). These linked observations that cancer cells retain functional oxidative phosphorylation machinery while driving metabolic reprogramming elsewhere suggest that the specific, simultaneous disruption of both pathways was a valid strategy for the development of colorectal cancer therapeutics.

The oncogenic transcriptional factors MYC proteins (c-Myc, n-Myc, l-Myc) are estimated to contribute to about 70% of all human cancers (13-15). Up-regulated MYC proteins, including c-Myc, drive tumorigenesis by promoting gene transcription, cellular metabolism, and cell proliferation (16-18). More than 90% of colorectal cancers are driven by an aberrant Wnt-β-catenin signaling pathway that upregulates Wnt-target genes including MYC (19). Pioneering studies that showed transient inactivation of MYC led to prolonged tumor remission in a conditional MYC-induced, transgenic, mouse tumor model (20). Systemic Myc inhibition in a Ras-induced lung cancer mouse model resulted in rapid tumor regression and reversible side-effects on normal regenerating tissues (21), a finding that demonstrated that MYC was a desirable therapeutic target in MYC-driven cancers. Although Myc was initially deemed as "undruggable" because it was an intrinsically disordered protein and lacked targetable, drug-binding pockets (22), direct and indirect pharmacological inhibitors of MYC emerged from studies with in vitro potencies in the micromolar concentration range (13,15,23,24). New agents and combination therapies with improved potency against MYC remain as an elusive but much needed therapy against colorectal cancers.

Our prior work revealed that a selective group of mitochondrial proton uncouplers that activated 5' adenosine monophosphate-activated protein kinase (AMPK), inhibited Wnt signaling, and reduced expression of Wnt signaling target genes including MYC (25). Metformin, best known as a low-potency ETC complex I inhibitor, reduced c-Myc in vitro and in vivo in certain prostate cancers (26). Phosphorylation of serine-62 in c-Myc by ERK or CDK kinases enhanced c-Myc stability, but the phosphorylation of c-Myc threonine-58 by GSK30 triggered serine-62 dephosphorylation by protein phosphatase 2A (PP2A), ubiquitination by the SCF-Fbw7 E3 ligase, and proteasomal destruction (13, 27). Polo kinase-1 (Plk1) also effected the phosphorylation of c-Myc at serine-62 that in turn enhanced c-Myc stability in colorectal and breast cancers (28). Plk1 inhibitors, including B12536 and volasertib, that is now in clinical trials (29), suppressed this undesired, growth-promoting c-Myc stabilization. These findings prompted our exploration of synergistic effects of reducing c-Myc stabilization in colorectal cancer through a combination of our newly identified ETC complex I and polo kinase-1 inhibitors.

SUMMARY

In accordance with the purposes and benefits described herein, novel indole-substituted quinolines are disclosed having use in treating various cancers, including c-MYC-driven cancers. In embodiments, the novel indole-substituted quinolines are administered in combination with polo kinase-1 inhibitors for treatment of cancer.

In one aspect of the disclosure, an indole-substituted quinoline (ISQ) is disclosed, comprising a compound having a structure according to Formula I:

I

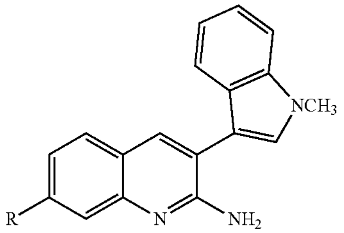

wherein R includes $N(R^1)_2$ or a substituted or unsubstituted six membered heterocycle including at least one nitrogen and wherein $R^1$ includes an alkyl. The compounds may in embodiments include a substituted piperidine including a structure according to Formula II:

II

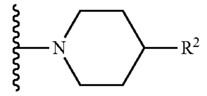

wherein $R^2$ includes branched or unbranched alkyl, hydroxyalkyl, alkoxyalkyl, cyano, aryl, arylalkyl, heteroaryl, or a combination thereof. In other embodiments, the compounds may include a substituted piperidine including a structure according to Formula III:

III

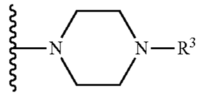

wherein $R^3$ includes a branched or unbranched alkyl. In embodiments, the compounds include the structures set forth herein in Tables 1-2.

In another aspect, the present disclosure describes a method of treating cancer, the method comprising administering the above-described compound to a subject in need thereof. The method may further include administering a polo-like kinase-1 (Plk1) inhibitor with the compound according to claim 1. In embodiments, the Plk1 and the compound are administered in synergistically effective amounts. One or more of the compounds set forth in Tables 1-2 may be selected. In embodiments, the Plk1 is selected from the group consisting of B12536, B16727 (volasertib), GSK461364, NMS-1286937 (onvansertib), and combinations. The cancer may be a c-MYC-driven cancer selected from one or more of breast cancer, lymphoma, melanoma, lung cancer, colorectal cancer, neural cancer, ovarian cancer, prostate cancer, and combinations.

In yet another aspect, a combination therapeutic is described, comprising an indole-substituted quinolone (ISQ) as described above. The ISQ may be combined with a Plk1 as described, in embodiments in synergistically effective amounts. The combination therapeutic may be formulated for treating cancers including c-MYC-driven cancers as described.

In the following description, there are shown and described several embodiments of the novel indole-substituted quinolones, methods for treatment of cancers using same, and combination therapeutics for treatment of cancers. As it should be realized, the bone biopsy system and related method are capable of other, different embodiments and their several details are capable of modification in various, obvious aspects all without departing from the bone biopsy system and method as set forth and described in the following claims. Accordingly, the drawings and descriptions should be regarded as illustrative in nature and not as restrictive.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIGS. 2A-B show images illustrating structure and activity relationship (SAR) studies. (A) Structure of ISQ analogs. (B) Effects of selected analogs on LS174T colon cancer cell proliferation. Cells were treated with ISQs at indicated concentrations for 5 days and counted. Data were shown as mean±SEM.

FIG. 10 shows graphs illustrating seahorse assay in Beas-2B cells. ETC complex V (ATPase) inhibitor oligomycin was replaced with ISQ-1 (top), ISQ-7 (bottom), or DMSO. OCR could not be rescued by the addition of FCCP in ISQ-1 and ISQ-7 treatment compared with oligomycin treatment respectively, showing that ISQ-1 and ISQ-7 did not inhibit ETC complex V.

Figure 1A:
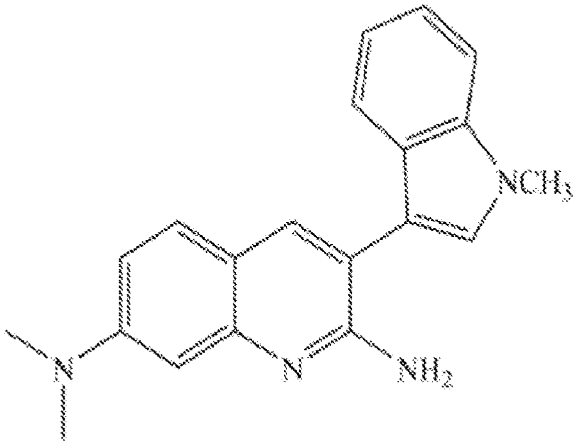
FIGS. 1A-E show graphs and images illustrating identification of indole-substituted quinolines as Wnt inhibitors and AMPK activators. (A) Structure of ISQ-1 (indole-substituted quinoline-1). (B) ISQ-1 inhibited proliferation of colon cancer cell line LS174T, prostate cancer cell line PC-3, sarcoma cell line SK-LMS-1 and liver cancer cell line HepG2 at nanomolar concentrations. Cells were treated with ISQ-1 at indicated concentrations for 5 days and counted. (C and D) ISQ-1 inhibited TOPFlash Wnt reporter and Wnt signaling target genes c-Myc and axin2. Cells stably expressing TOPFlash Wnt reporter were treated for 24 hours and luciferase luminescence was analyzed (C). (E) ISQ-1 activated AMPK and increased AMPK substrate ACC phosphorylation in LS174T cells.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims, unless the context clearly dictates otherwise. Thus, for example, reference to "a polypeptide" includes one or more of such polypeptides, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, ElZ specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The terms "alkoxy" and "alkoxyl" as used herein to refer to an alkyl or cycloalkyl group bonded through an ether linkage; that is, an "alkoxy" group can be defined as $—OR^1$ where $R^1$ is alkyl or cycloalkyl as defined above. "Alkoxy" also includes polymers of alkoxy groups as just described; that is, an alkoxy can be a polyether such as $—OR^1—OR^2$ or $—OR^1—(OR^2)_a—OR^3$, where "a" is an integer of from 1 to 200 and $R^1$, $R^2$, and $R^3$ are alkyl and/or cycloalkyl groups.

The term "alkyl" as used herein is a branched or unbranched saturated hydrocarbon group, such as methyl, ethyl, propyl, isopropyl, butyl, isobutyl, s-butyl, i-butyl, pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. Unless explicitly stated otherwise, the alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "alkoxyalkyl" specifically refers to an alkyl group that is substituted with one or more alkoxy groups (e.g., $—CH_2OCH_3$), as described below. The term "arylalkyl" specifically refers to an alkyl group that is substituted with one or more aryl groups (e.g., —$CH_2C_6H_5$), as described below. When "alkyl" is used in one instance and a specific term such as "hydroxyalkyl" is used in another, it is not meant to imply that the term "alkyl" does not also refer to specific terms such as "hydroxyalkyl" and the like.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "cyano" and "nitrile" as used herein are interchangeably represented by the formula —CN.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

Provided herein are compounds and methods for treating cancer. In some embodiments, the compound is a small-molecule compound. In some embodiments, the compound includes an indole-substituted quinoline (ISQ). For example, in some embodiments, the ISQ includes any compound having a structure according to Formula I, or analogs, derivatives, or salts thereof.

I

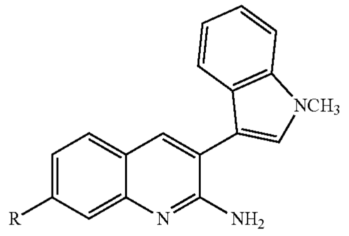

Where R is $N(R^1)_2$ or a substituted or unsubstituted heterocycle including at least one nitrogen, and $R^1$ is an alkyl. In some embodiments, R includes $N(CH_3)_2$, unsubstituted piperidine, unsubstituted piperazine, substituted piperidine, or substituted piperazine. In some embodiments, the substituted piperidine includes a structure according to Formula II, or analogs, derivatives, or salts thereof:

II

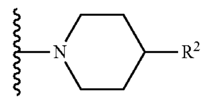

Where $R^2$ is branched or unbranched alkyl, hydroxyalkyl, alkoxyalkyl, cyano, aryl, arylalkyl, heteroaryl, or a combination thereof. In some embodiments, the substituted piperazine includes a structure according to Formula III, or analogs or derivatives thereof:

III

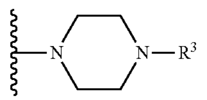

Where $R^3$ is branched or unbranched alkyl. For example, in some embodiments, the compound according to Formula I includes one or more of the compounds shown in Table 1, or analogs or derivatives thereof.

TABLE 1

| ID | R | STRUCTURE |
|---|---|---|
| ISQ-1 | $N(R^1)_2$ | 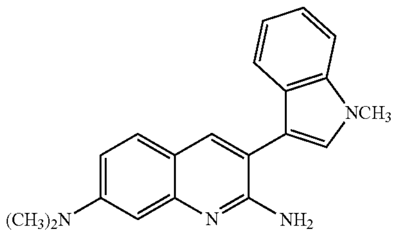 |

TABLE 1-continued
| ID | R | STRUCTURE |
|---|---|---|
| ISQ-2 | unsubstituted piperidine | 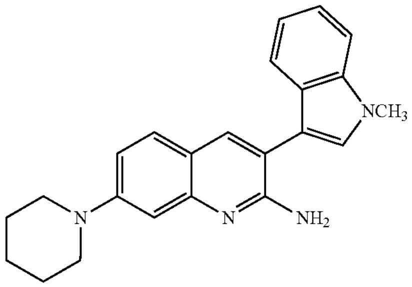 [SMILES: Cn1cc(-c2cc3ccc(N4CCCCC4)cc3nc2N)c2ccccc21] |
| ISQ-3 | substituted piperazine where $R^3$ is unbranched alkyl | 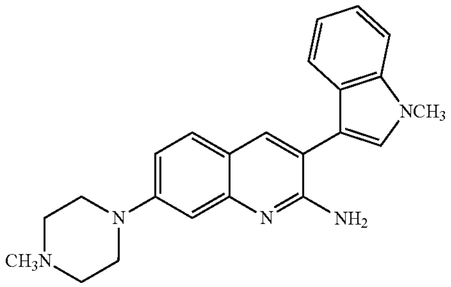 |
| ISQ-4 | substituted piperidine where $R^2$ is branched alkyl | 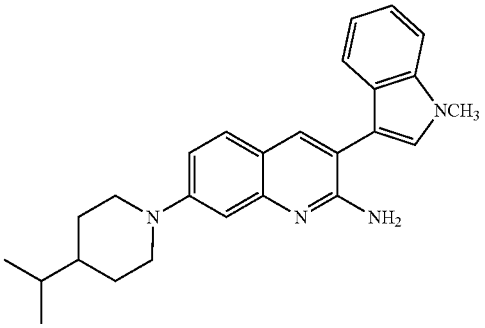 [SMILES: CC(C)C1CCN(c2ccc3cc(-c4cn(C)c5ccccc45)c(N)nc3c2)CC1] |
| ISQ-5 | substituted piperidine where $R^2$ is arylalkyl | 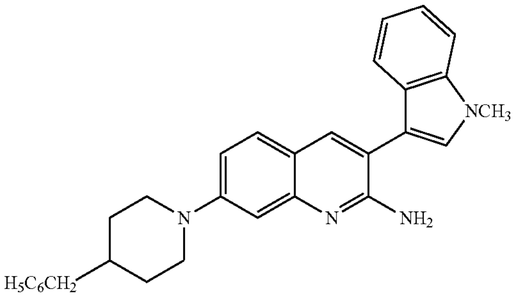 |
| ISQ-6 | substituted piperidine where $R^2$ is aryl | 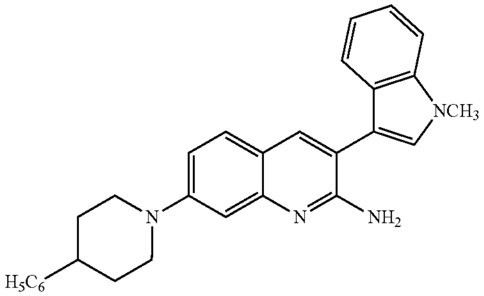 |

TABLE 1-continued

| ID | R | STRUCTURE |
|---|---|---|
| ISQ-7 | substituted piperidine where $R^2$ is cyano | 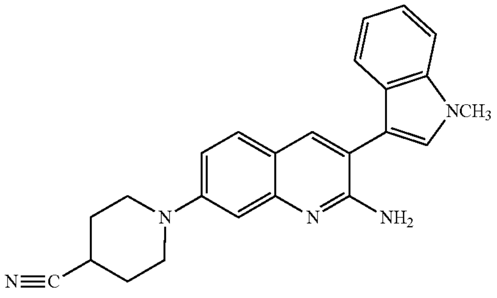 [SMILES: Cn1cc(-c2cc3ccc(N4CCC(C#N)CC4)cc3nc2N)c2ccccc21] |
| ISQ-8 | substituted piperidine where $R^2$ is hydroxyalkyl | 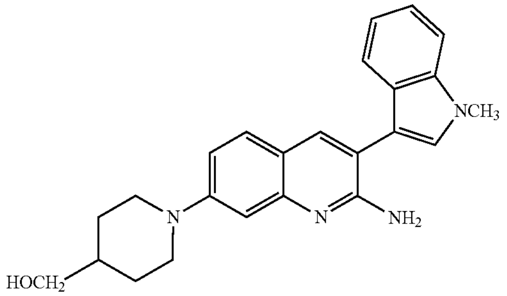 |
| ISQ-9 | substituted piperidine where $R^2$ is alkoxyalkyl | 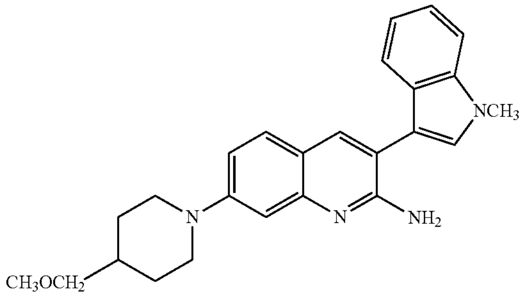 |
| ISQ-10 | substituted piperidine where $R^2$ is heteroaryl | 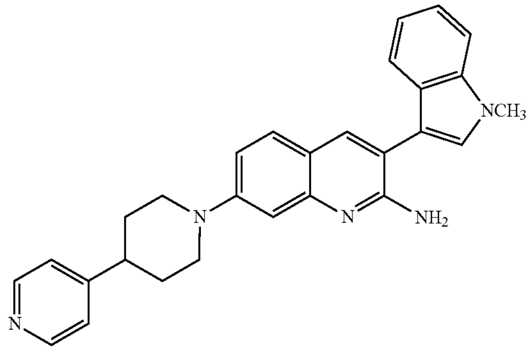 [SMILES: Cn1cc(-c2cc3ccc(N4CCC(c5ccncc5)CC4)cc3nc2N)c2ccccc21] |

In some embodiments, one or more of the compounds disclosed herein inhibit Wnt signaling and/or activate adenosine monophosphate kinase (AMPK), a cellular, energy-homeostasis, master regulator. Additionally or alternatively, in some embodiments, one or more of the compounds disclosed herein inhibit complex I (i.e., NADH ubiquinone oxidoreductase) in the mitochondrial, electron transport chain (ETC). Accordingly, in some embodiments, the compounds disclosed herein act as potent inhibitors of several cancer cell lines such as, but not limited to, colorectal cancer. In some embodiments, when combined with a polo-like kinase-1 (Plk1) inhibitor, the one or more compounds disclosed herein provide synergistic depletion of oncogenic c-Myc protein level and induce strong tumor remission. Suitable Plk1 inhibitors include, but are not limited to, BI2536 and BI6727.

Also provided herein are methods of treating cancer using one or more of the compounds disclosed herein. In some embodiments, the method includes administering one or more of the compounds according to Formula I to a subject in need thereof. For example, in some embodiments, the method includes administering one or more of the compounds in Table 1 to a subject in need thereof. In some embodiments, the method includes administering a polo-like kinase-1 (Plk1) inhibitor and one or more of the compounds concurrently according to Formula I to a subject in need thereof. Without wishing to be bound by theory, it is believed that the combined administration of a Plk1 inhibitor and one or more of the compounds according to Formula I provides synergistic depletion of oncogenic c-Myc protein levels and induces strong tumor remission. Accordingly, in some embodiments, the method disclosed herein is suitable for treatment of any c-Myc driven cancer such as, but not limited to, colon cancer, liver cancer, and prostate cancer.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Developing effective treatments for colorectal cancers through combinations of small-molecule approaches and immunotherapies present intriguing possibilities for managing these otherwise intractable cancers. During a broad-based, screening effort against multiple colorectal cancer cell lines, indole-substituted quinolines (ISQs), such as $N^7$,$N^7$-dimethyl-3-(1-methyl-1H-indol-3-yl)quinoline-2,7-diamine (ISQ-1), were identified as potent in vitro inhibitors of several cancer cell lines. It was found that ISQ-1 inhibited Wnt signaling, a main driver in the pathway governing colorectal cancer development, and ISQ-1 also activated adenosine monophosphate kinase (AMPK), a cellular energy-homeostasis master regulator. The effect of ISQs on cell metabolism was explored as well. Seahorse assays measuring oxygen consumption rate (OCR) indicated that ISQ-1 inhibited complex I (i.e., NADH ubiquinone oxidoreductase) in the mitochondrial, electron transport chain (ETC). In addition, ISQ-1 treatment showed remarkable synergistic depletion of oncogenic c-Myc protein level in vitro and induced strong tumor remission in vivo when administered together with B12536, a polo-like kinase-1 (Plk1) inhibitor. This Example supports the potential value of dual drug therapies targeting the ETC and Plk-1 for the treatment of c-Myc-driven cancers.

Results

Figure 1B:
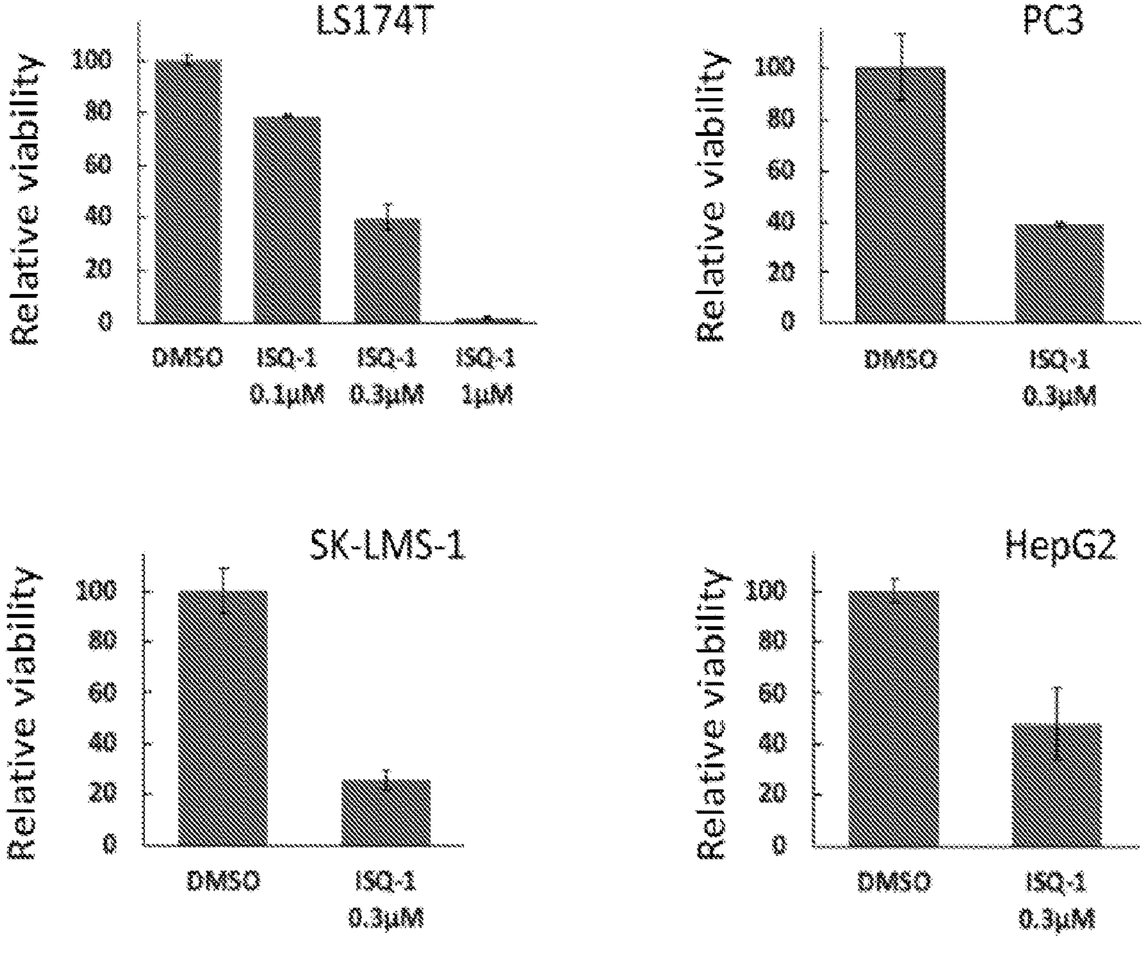
Figure 1C:
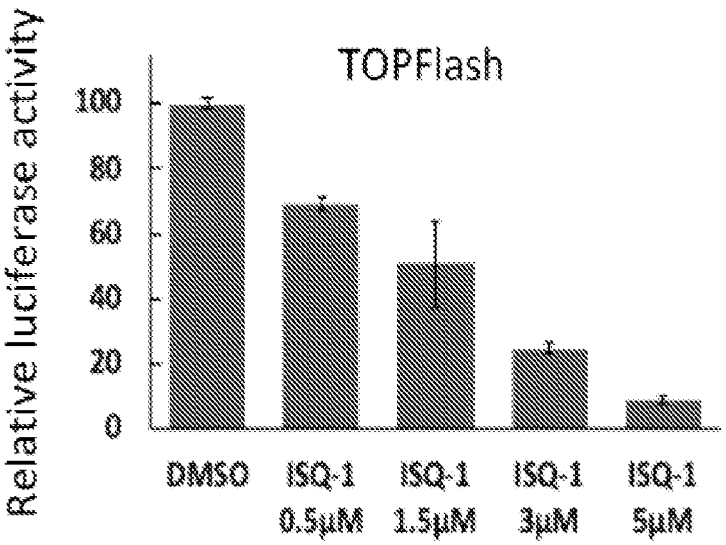
Figure 1D:
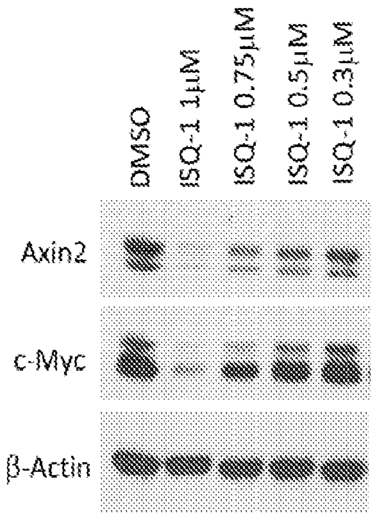
Figure 1E:
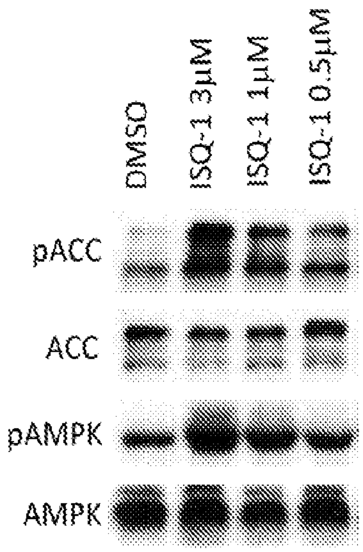

Deregulated Wnt signaling is the main driver of colorectal cancer initiation and progression. The long-standing efforts by the present inventors to develop drug candidates for the treatment of colorectal cancers (30-34) focused on the Wnt pathway and led to a family of aryl-substituted quinolines called "arylquins." Using a combination of a Wnt reporter assay and an AMPK activation assay, indole-substituted quinolines (ISQs) bearing C-3 N-methylindole groups were identified, such as $N^7$,$N^7$-dimethyl-3-(1-methyl-1H-indol-3-yl)quinoline-2,7-diamine (ISQ-1) (FIG. 1A), that inhibited in vitro cell growth of colon cancer LS174T, prostate cancer PC-3, sarcoma SK-LMS-1, and liver cancer HepG2 cell lines at nanomolar concentrations (FIG. 1B). It was found that ISQ-1 also inhibited Wnt signaling target genes including c-Myc and axin2 and activated AMPK in a dose-dependent manner (FIGS. 1C-1E). The synthesis and structural characterization of ISQs are described in Materials and Methods section.

A study of structure-activity relationships (SAR) using cell proliferation assays as a readout quickly revealed the importance of the N,N-dialkylamino group at C-7 in the ISQ pharmacophore (i.e., R in FIG. 2A), an amino group at C-2 and an N-methyl-3-indolyl group at C-3. The substitution of other aryl or heteroaryl groups for the N-methyl-3-indolyl group in ISQs were unrewarding in terms of identifying inhibitors with $IC_{50}$ values less than 100 nM. Variations, however, at the C-7 position in the ISQs produced a series of important inhibitors. Initial studies of the percentage inhibition of LS174T cell proliferation at 500 nM, as shown in FIG. 2B, indicated that ISQs bearing a simple N,N-dimethylamino group at C-7 (i.e., ISQ-1) were more active than those bearing N-piperidinyl (i.e., ISQ-2), N-alkylpiperazinyl (i.e., ISQ-3, 4 and 5), or N-phenylpiperazinyl groups (i.e., ISQ-6). In contrast, however, ISQs bearing additional oxygen or nitrogen atoms in N-alkylpiperazinyl groups, as in the N-cyano, N-hydroxymethyl, or N-methoxymethylpiperazinyl analogs (ISQ-7, 8 and 9, respectively), or an additional nitrogen atom in the N-arylpiperazinyl group, as in N-(4-pyridyl)piperazinyl analog (ISQ-10), possessed inhibitory activity comparable to the N,N-dimethylamino group in ISQ-1 at 500 nM. Dose response studies for these ISQs as inhibitors in these cell proliferation assays revealed that the most promising of these ISQ inhibitors with $IC_{50}$ values in the 100 nM range were those in which the piperazinyl group at C-3 possessed heteroatom-substituted groups (i.e., ISQ-7, 8, 9 and 10). The results for additional studies of the percentage inhibition of LS174T cell proliferation for ISQ-1 and analogs thereof are shown in Tables 2-3.

TABLE 2

VMS-7-25 Analogs Inhibition % on LS174T cells Proliferation

| Compounds | Nomen-clature | Structure | 62 nM | 125 nM | 250 nM | 500 nM |
|---|---|---|---|---|---|---|
| VMS-7-25 | ISQ-1 | 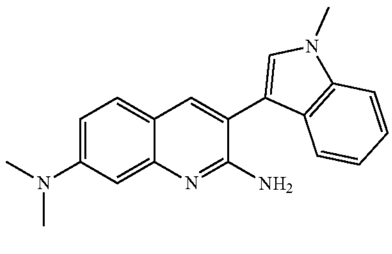 [SMILES: CN(C)c1ccc2cc(-c3cn(C)c4ccccc34)c(N)nc2c1] | 16 ± 2 | 22 ± 5 | 38 ± 2.2 | 91 ± 4.3 |

TABLE 2-continued
VMS-7-25 Analogs Inhibition % on LS174T cells Proliferation
| Compounds | Nomen-clature | Structure | 62 nM | 125 nM | 250 nM | 500 nM |
|---|---|---|---|---|---|---|
| LMK-5-288 | ISQ-2 | 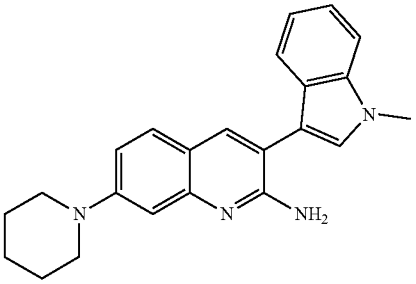 [SMILES: Cn1cc(-c2cc3ccc(N4CCCCC4)cc3nc2N)c2ccccc21] | 8.2 ± 5.6 | 28 ± 4.6 | 55 ± 0.5 | 97 ± 0.4 |
| LMK-6-53 | ISQ-3 | 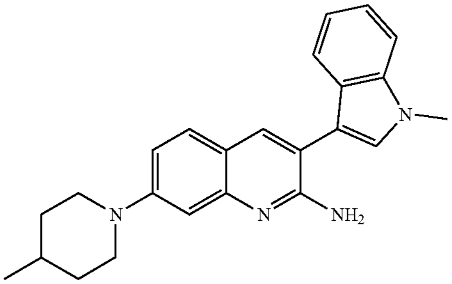 | ND | ND | 27 ± 14 | 89 ± 2.1 |
| LMK-6-82 | ISQ-4 | 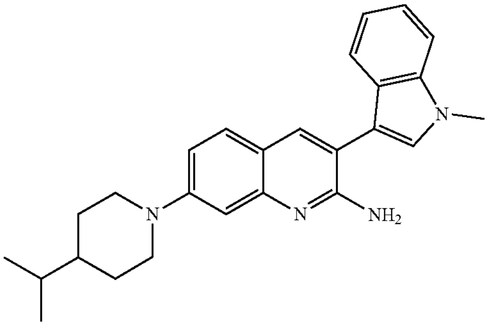 [SMILES: CC(C)C1CCN(c2ccc3cc(-c4cn(C)c5ccccc45)c(N)nc3c2)CC1] | ND | ND | ND | 36 ± 0.9 |
| LMK-6-84 | | 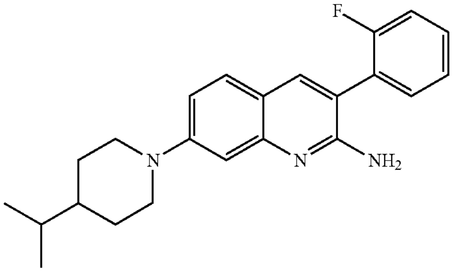 [SMILES: CC(C)C1CCN(c2ccc3cc(-c4ccccc4F)c(N)nc3c2)CC1] | ND | ND | ND | 79 ± 5.7 |
| LMK-6-88 | ISQ-6 | 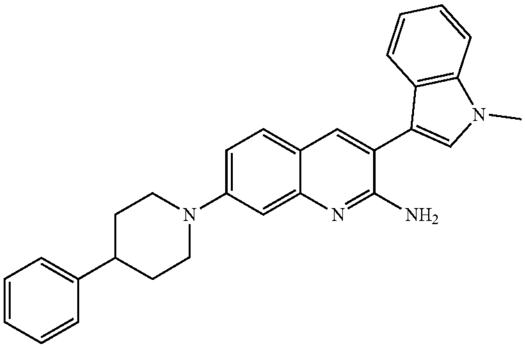 [SMILES: Cn1cc(-c2cc3ccc(N4CCC(c5ccccc5)CC4)cc3nc2N)c2ccccc21] | ND | ND | ND | 56 ± 13.1 |

TABLE 2-continued
VMS-7-25 Analogs Inhibition % on LS174T cells Proliferation
| Compounds | Nomen-clature | Structure | 62 nM | 125 nM | 250 nM | 500 nM |
|---|---|---|---|---|---|---|
| LMK-6-89 | | 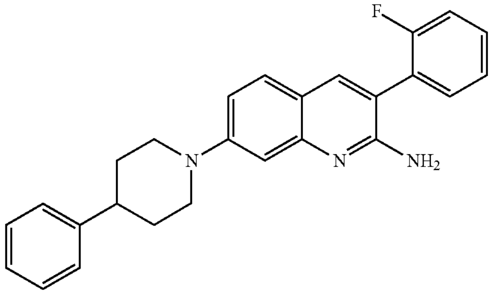 [SMILES: Nc1nc2cc(N3CCC(c4ccccc4)CC3)ccc2cc1-c1ccccc1F] | 2 ± 3 | 20 ± 0.6 | 23 ± 3.8 | 89 ± 1 |
| LMK-6-90 | ISQ-5 | 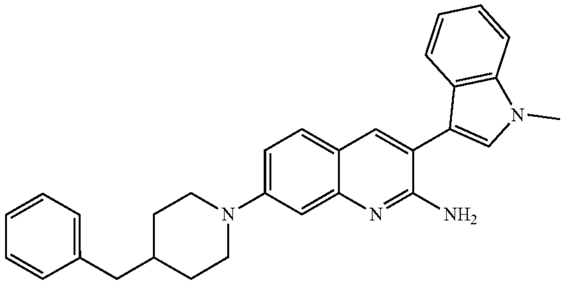 [SMILES: Cn1cc(-c2cc3ccc(N4CCC(Cc5ccccc5)CC4)cc3nc2N)c2ccccc21] | ND | ND | ND | 21 ± 3.9 |
| LMK-6-91 | | 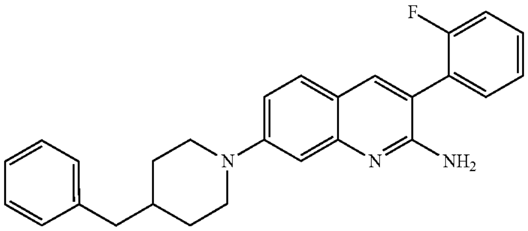 [SMILES: Nc1nc2cc(N3CCC(Cc4ccccc4)CC3)ccc2cc1-c1ccccc1F] | ND | ND | ND | 14 ± 1.2 |
| LMK-6-98 | ISQ-7 | 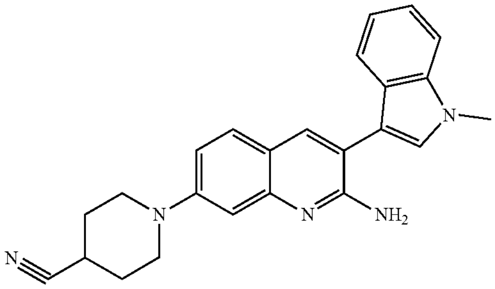 [SMILES: Cn1cc(-c2cc3ccc(N4CCC(C#N)CC4)cc3nc2N)c2ccccc21] | 19 ± 5.5 | 89 ± 0.2 | 98 ± 0.6 | 97 ± 0.7 |
| LMK-6-99 | | 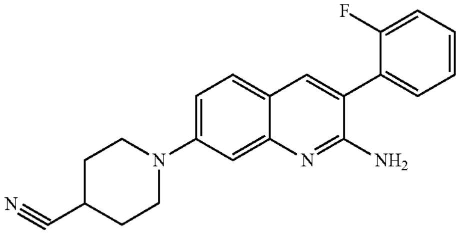 [SMILES: N#CC1CCN(c2ccc3cc(-c4ccccc4F)c(N)nc3c2)CC1] | 2 ± 0.2 | 9 ± 2.2 | 17 ± 0.1 | 64 ± 3.5 |

TABLE 2-continued
| VMS-7-25 Analogs Inhibition % on LS174T cells Proliferation | | | | | | |
|---|---|---|---|---|---|---|
| Compounds | Nomen-clature | Structure | 62 nM | 125 nM | 250 nM | 500 nM |
| LMK-6-102 | ISQ-10 | 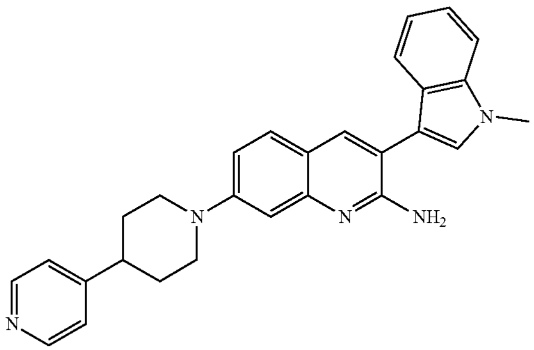 [SMILES: Cn1cc(-c2cc3ccc(N4CCC(c5ccncc5)CC4)cc3nc2N)c2ccccc21] | 21 ± 5.7 | 84 ± 2.7 | 99 ± 13.1 | 99 ± 0.1 |
| LMK-6-108 | ISQ-9 | 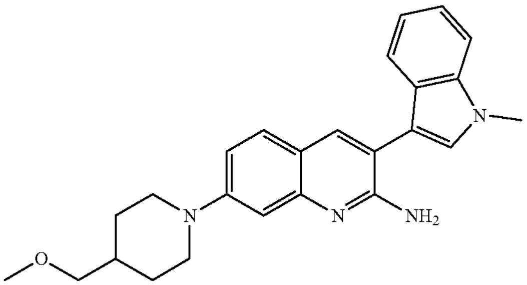 | 12 ± 1.9 | 55 ± 2.3 | 98 ± 0 | 99 ± 0.1 |
| LMK-6-109 | | 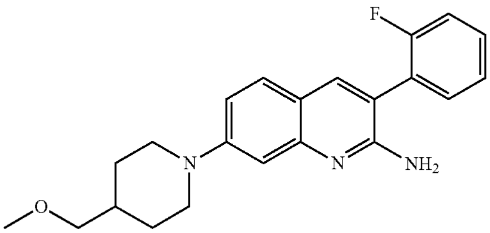 [SMILES: COCC1CCN(c2ccc3cc(-c4ccccc4F)c(N)nc3c2)CC1] | 16 ± 8.4 | 29 ± 0.3 | 70 ± 8.8 | 94 ± 0.1 |
| LMK-6-116 | ISQ-8 | 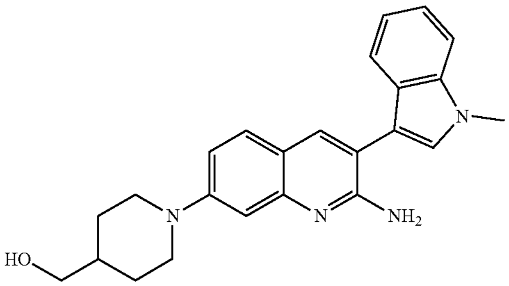 [SMILES: Cn1cc(-c2cc3ccc(N4CCC(CO)CC4)cc3nc2N)c2ccccc21] | 20 ± 9 | 59 ± 2.7 | 97 ± 0.2 | 98 ± 0.6 |
| LMK-6-117 | | 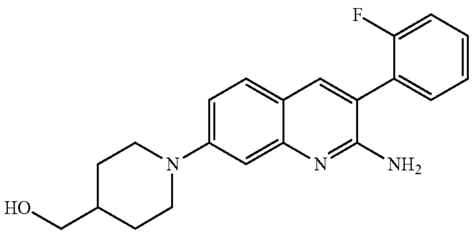 [SMILES: Nc1nc2cc(N3CCC(CO)CC3)ccc2cc1-c1ccccc1F] | 12 ± 1.4 | 12 ± 0.7 | 32 ± 10.5 | 59 ± 0.3 |

TABLE 3
VMS-7-25 Analogs Inhibition % on LS174T cells Proliferation
| Sample ID | Structure | 3 uM Inhib. % | 3 uM std | 1 uM Inhib. % | 1 uM std | 0.3 uM Inhib. % | 0.3 uM std |
|---|---|---|---|---|---|---|---|
| VMS-4-57 | 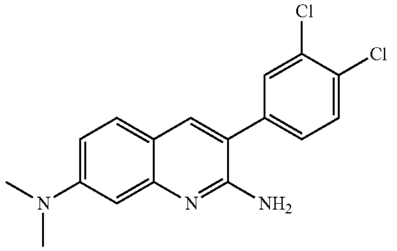 [SMILES: CN(C)c1ccc2cc(-c3ccc(Cl)c(Cl)c3)c(N)nc2c1] | 74.3 | 0.09 | 57.8 | 8.2 | 26.7 | 2.4 |
| VMS-4-103 | 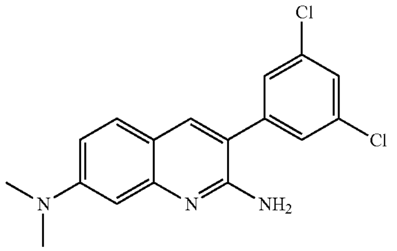 [SMILES: CN(C)c1ccc2cc(-c3cc(Cl)cc(Cl)c3)c(N)nc2c1] | 86.4 | 1.66 | | | | |
| VMS-7-1 | 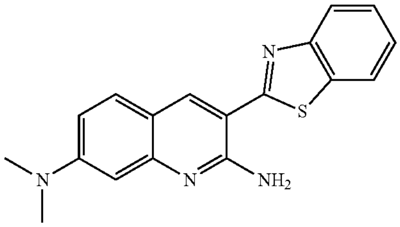 [SMILES: CN(C)c1ccc2cc(-c3nc4ccccc4s3)c(N)nc2c1] | 95.3 | 0.64 | | | | |
| VMS-7-3 | 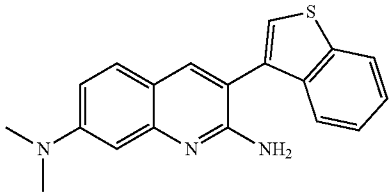 [SMILES: CN(C)c1ccc2cc(-c3csc4ccccc34)c(N)nc2c1] | 96.7 | 1.48 | | | | |
| VMS-7-7 | 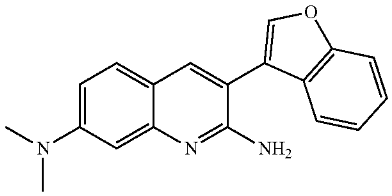 [SMILES: CN(C)c1ccc2cc(-c3coc4ccccc34)c(N)nc2c1] | 96.8 | 0.51 | 97.8 | 0.1 | 87.2 | 2 |
| VMS-7-25 | 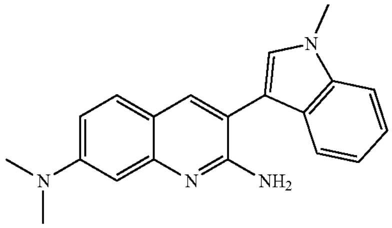 [SMILES: CN(C)c1ccc2cc(-c3cn(C)c4ccccc34)c(N)nc2c1] | 99.3 | 0.57 | 92.7 | 3 | 83.9 | 2.3 |

TABLE 3-continued
| VMS-7-25 Analogs Inhibition % on LS174T cells Proliferation | | | | | | | |
|---|---|---|---|---|---|---|---|
| | | 3 uM | | 1 uM | | 0.3 uM | |
| Sample ID | Structure | Inhib. % | std | Inhib. % | std | Inhib. % | std |
| VMS-7-29 | 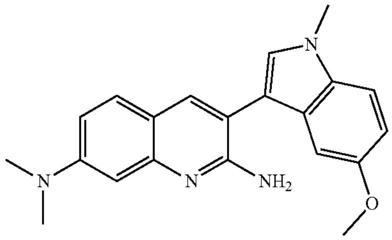 [SMILES: COc1ccc2c(c1)c(-c1cc3ccc(N(C)C)cc3nc1N)cn2C] | 99.3 | 0.33 | | | | |
| LMK-5-52 | 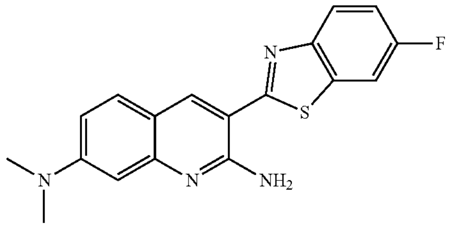 [SMILES: CN(C)c1ccc2cc(-c3nc4ccc(F)cc4s3)c(N)nc2c1] | 97.0 | 0.67 | | | | |
| LMK-5-55 | 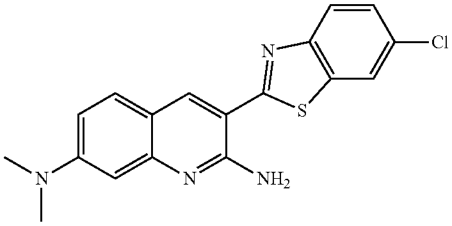 [SMILES: CN(C)c1ccc2cc(-c3nc4ccc(Cl)cc4s3)c(N)nc2c1] | 97.6 | 0.40 | | | | |
| LMK-5-60 | 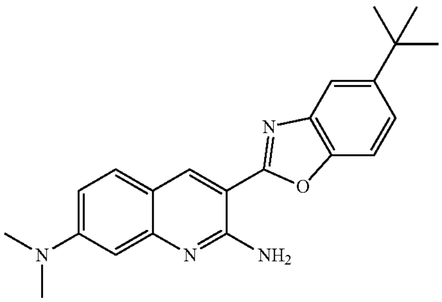 [SMILES: CN(C)c1ccc2cc(-c3nc4cc(C(C)(C)C)ccc4o3)c(N)nc2c1] | 91.5 | 1.23 | | | | |
| LMK-5-62 | 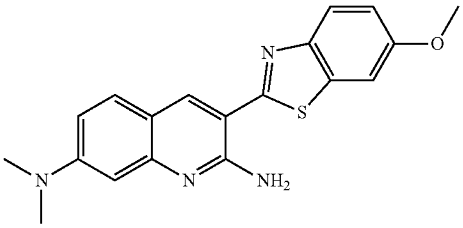 | 85.5 | 1.60 | | | | |

TABLE 3-continued
VMS-7-25 Analogs Inhibition % on LS174T cells Proliferation
| Sample ID | Structure | 3 uM Inhib. % | 3 uM std | 1 uM Inhib. % | 1 uM std | 0.3 uM Inhib. % | 0.3 uM std |
|---|---|---|---|---|---|---|---|
| LMK-5-66 | 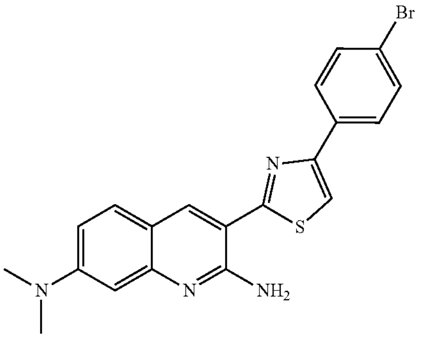 [SMILES: CN(C)c1ccc2cc(-c3nc(-c4ccc(Br)cc4)cs3)c(N)nc2c1] | 98.9 | 1.08 | 45.0 | 1.78 | | |
| LMK-5-67 | 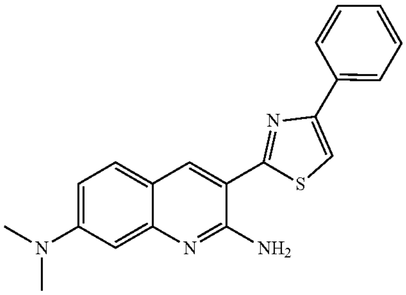 [SMILES: CN(C)c1ccc2cc(-c3nc(-c4ccccc4)cs3)c(N)nc2c1] | 99.8 | 0.03 | 96.9 | 0.71 | | |
| LMK-5-68 | 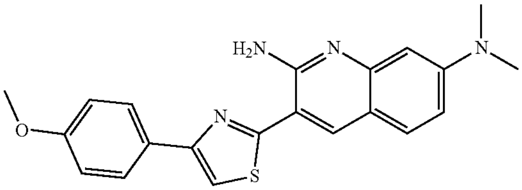 | 94.3 | 0.10 | 24.2 | 0.92 | | |
| VMS-8-67 | 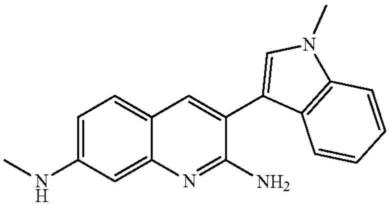 [SMILES: CNc1ccc2cc(-c3cn(C)c4ccccc34)c(N)nc2c1] | 96.9 | 0.37 | | | | |
| VMS-8-65 | 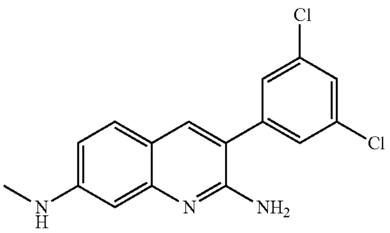 [SMILES: CNc1ccc2cc(-c3cc(Cl)cc(Cl)c3)c(N)nc2c1] | 97.2 | 0.27 | | | | |

TABLE 3-continued
VMS-7-25 Analogs Inhibition % on LS174T cells Proliferation
| Sample ID | Structure | 3 uM Inhib. % | 3 uM std | 1 uM Inhib. % | 1 uM std | 0.3 uM Inhib. % | 0.3 uM std |
|---|---|---|---|---|---|---|---|
| LMK-5-276 | 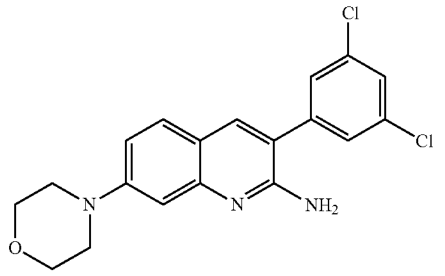 [SMILES: Nc1nc2cc(N3CCOCC3)ccc2cc1-c1cc(Cl)cc(Cl)c1] | 65.2 | 4.54 | 35.0 | 1.23 | | |
| LMK-5-278 | 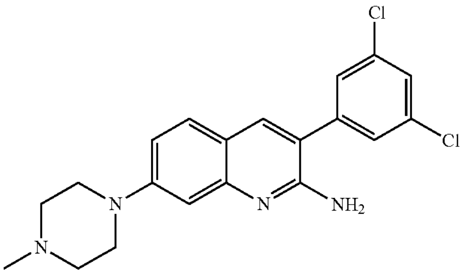 [SMILES: CN1CCN(c2ccc3cc(-c4cc(Cl)cc(Cl)c4)c(N)nc3c2)CC1] | 87.7 | 0.18 | 27.9 | 4.60 | | |
| LMK-5-279 | 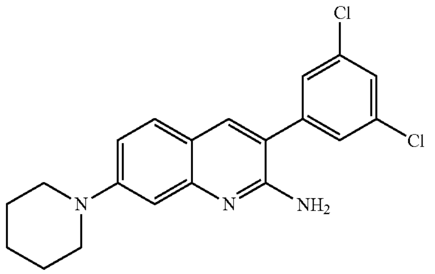 [SMILES: Nc1nc2cc(N3CCCCC3)ccc2cc1-c1cc(Cl)cc(Cl)c1] | 87.6 | 1.17 | 46.6 | 5.77 | | |
| LMK-5-280 | 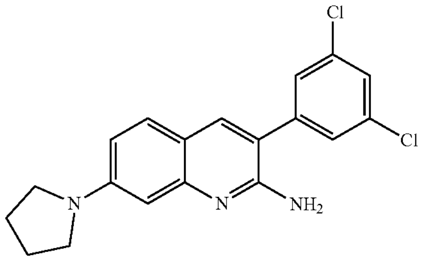 [SMILES: Nc1nc2cc(N3CCCC3)ccc2cc1-c1cc(Cl)cc(Cl)c1] | 97.7 | 0.27 | 93.1 | 0.8 | 31 | 6.4 |
| LMK-5-281 | 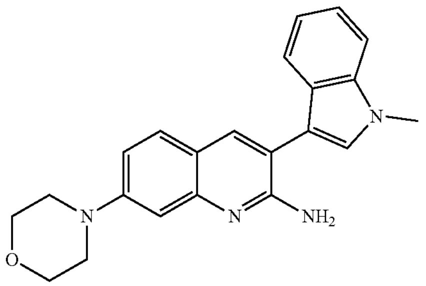 [SMILES: Cn1cc(-c2cc3ccc(N4CCOCC4)cc3nc2N)c2ccccc21] | 98.1 | 0.54 | 93.7 | 1.6 | 30.9 | 4.9 |

TABLE 3-continued

VMS-7-25 Analogs Inhibition % on LS174T cells Proliferation

| Sample ID | Structure | 3 uM Inhib. % | 3 uM std | 1 uM Inhib. % | 1 uM std | 0.3 uM Inhib. % | 0.3 uM std |
|---|---|---|---|---|---|---|---|
| LMK-5-282 | 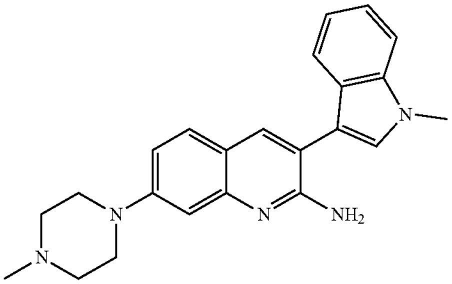 | 83.7 | 6.56 | 25.2 | 0.61 | | |
| LMK-5-284 | 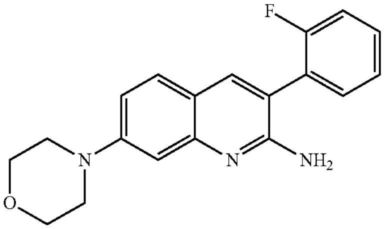 [SMILES: Nc1nc2cc(N3CCOCC3)ccc2cc1-c1ccccc1F] | 85.6 | 3.53 | 20.6 | 11.35 | | |
| LMK-5-286 | 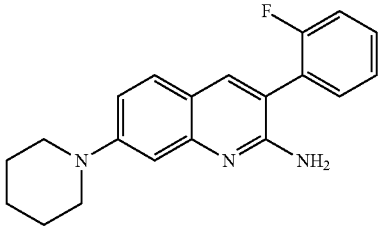 [SMILES: Nc1nc2cc(N3CCCCC3)ccc2cc1-c1ccccc1F] | 97.0 | 0.07 | 96.0 | 2.1 | 21.9 | 13.2 |
| LMK-6-53 | 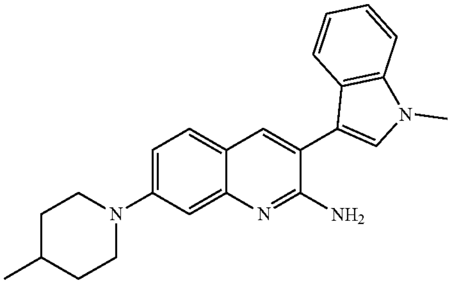 | 99.7 | 0.07 | 95.5 | 1.2 | 73.9 | 1.2 |

Figure 3A:
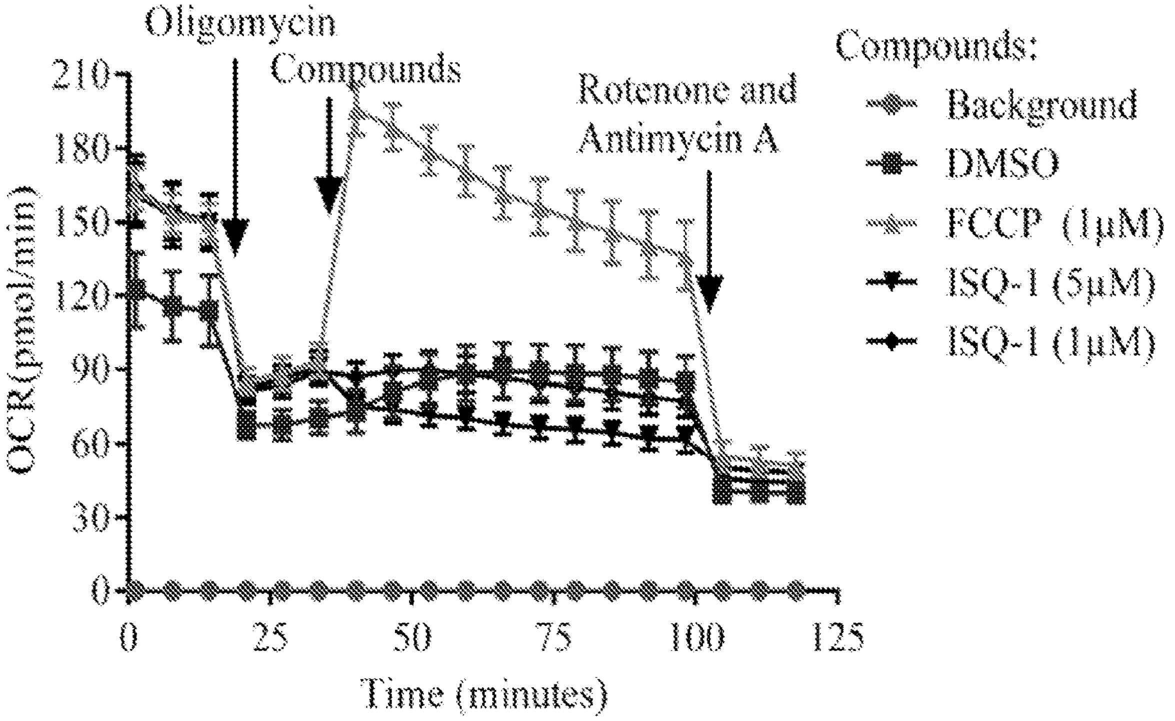
FIGS. 3A-D show graphs illustrating that ISQ-1 inhibited mitochondrial ETC (electron transport chain) complex I in LS174T cells. (A) Seahorse assay—A classic uncoupler FCCP was replaced with ISQ-1 or DMSO. ISQ-1, unlike FCCP, failed to increase OCR and was not an uncoupler. (B) Seahorse assay. ETC complex V (ATPase) inhibitor oligomycin was replaced with ISQ-1 or DMSO. OCR could not be rescued by the addition of FCCP in ISQ-1 treatment compared with oligomycin treatment, indicating that ISQ-1 did not inhibit ETC complex V. (C) Seahorse assay. ETC complex complexes I/III inhibitors rotenone/antimycin were replaced with ISQ-1 or DMSO. ISQ-1 showed similar inhibitory effects on OCR compared with rotenone/antimycin, suggesting that ISQ-1 inhibited ETC complex I or III. (D) Mitochondrial ETC complex activity measurements using PMP-permeabilized cells. PMP selectively disrupted cell membrane but left mitochondrial membrane intact. ISQ-1 inhibited OCR to a similar extent with rotenone, a complex I inhibitor. This inhibition was bypassed by adding the complex II substrate succinate, showing that ISQ-1 inhibited ETC complex I.
Figure 9:
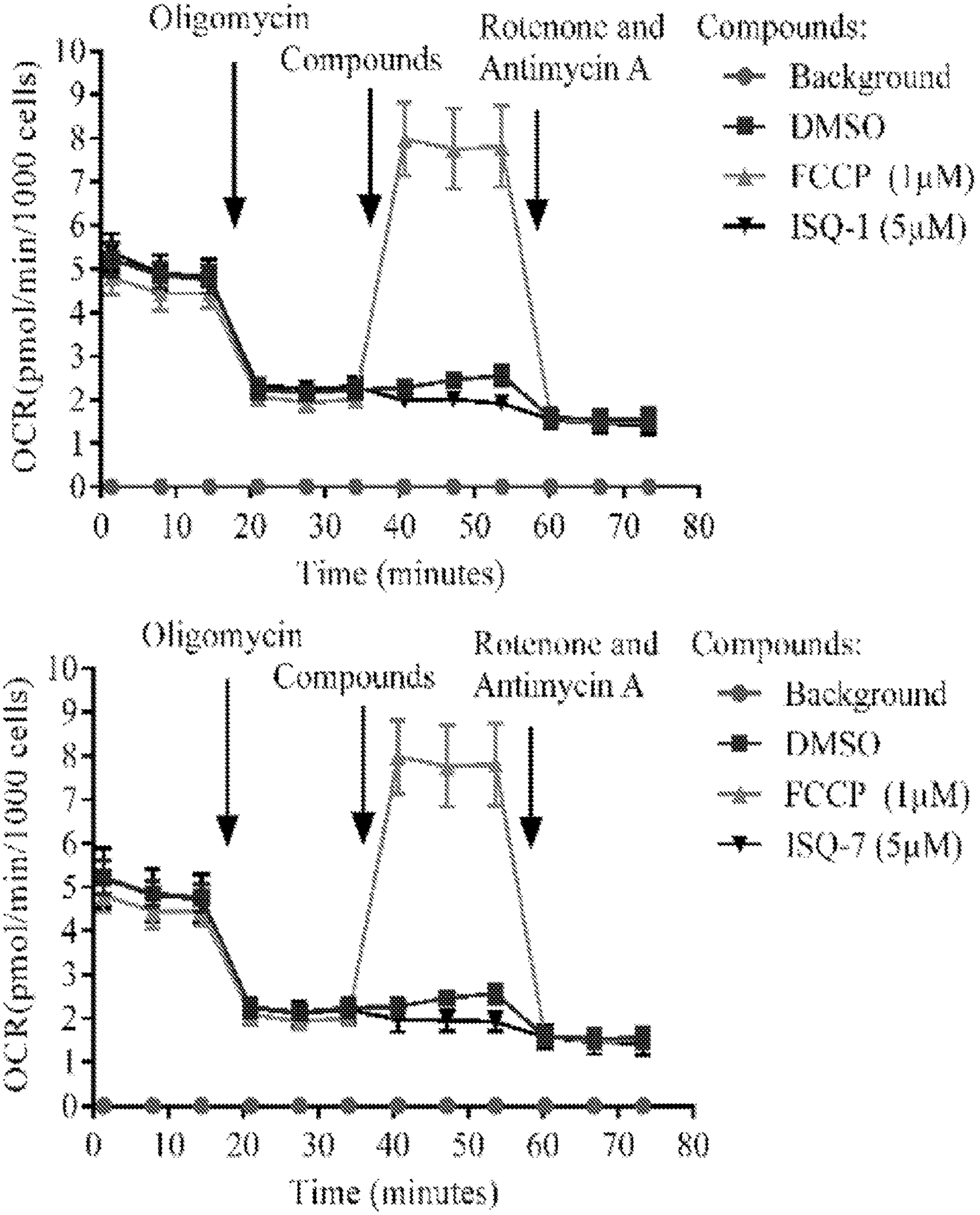
FIG. 9 shows graphs illustrating seahorse assay in Beas-2B cells. A classic uncoupler FCCP was replaced with ISQ-1 (top), ISQ-7 (bottom), or DMSO. ISQ-1 and ISQ-7 failed to increase OCR as FCCP did, indicating that ISQ-1 and ISQ-7 were no uncouplers.

Previous work by the present inventors revealed that certain mitochondrial proton uncouplers that activated AMPK also inhibited Wnt signaling by disrupting energy supply for signaling transduction. The dual effects of ISQs on Wnt signaling and AMPK activation prompted an investigation of the effects of ISQs on oxidative phosphorylation using Agilent Seahorse assays. Known uncoupler N-(4-(trifluoromethoxy)phenyl)carbonohydrazonoyl dicyanide (FCCP) was initially compared with ISQ-1 in dimethyl sulfoxide (DMSO) or the vehicle alone in a standard Seahorse assay. Unlike known mitochondrial proton uncouplers such as FCCP that activated AMPK, ISQ-1 failed to rescue oligomycin-inhibited oxygen consumption rate (OCR) and thus was not a mitochondrial proton uncoupler (FIGS. 3A and 9).

Figure 3B:
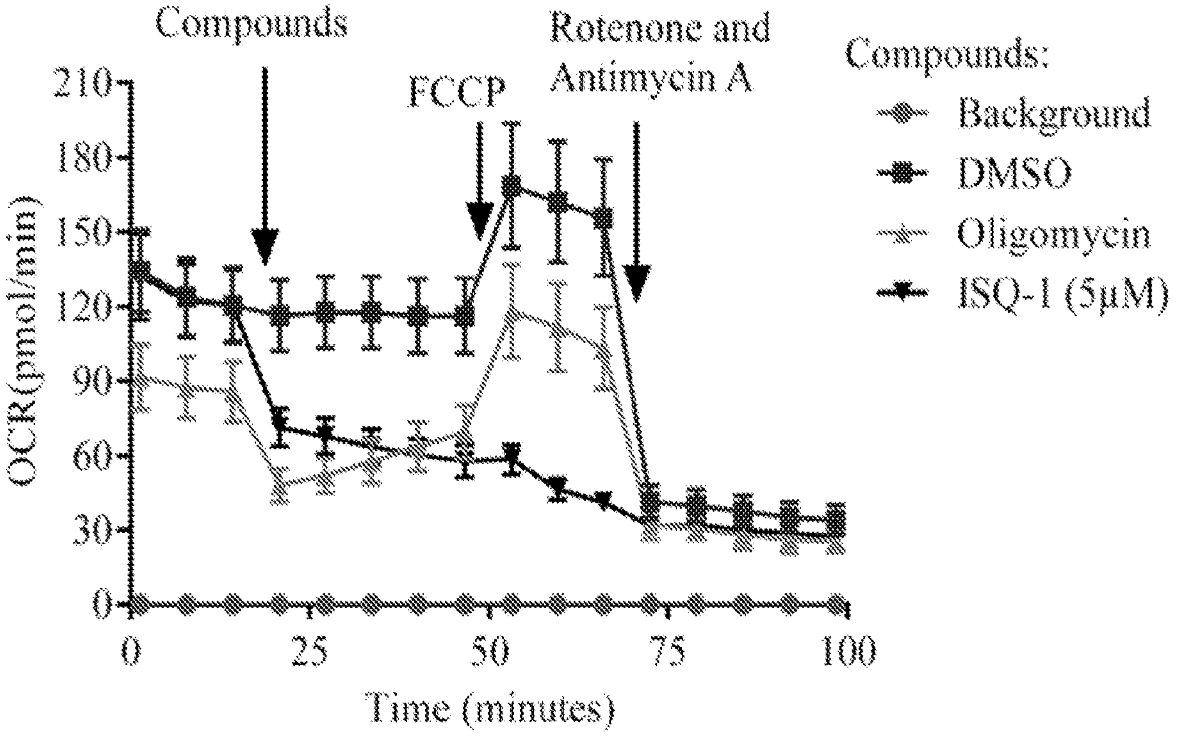
Figure 3C:
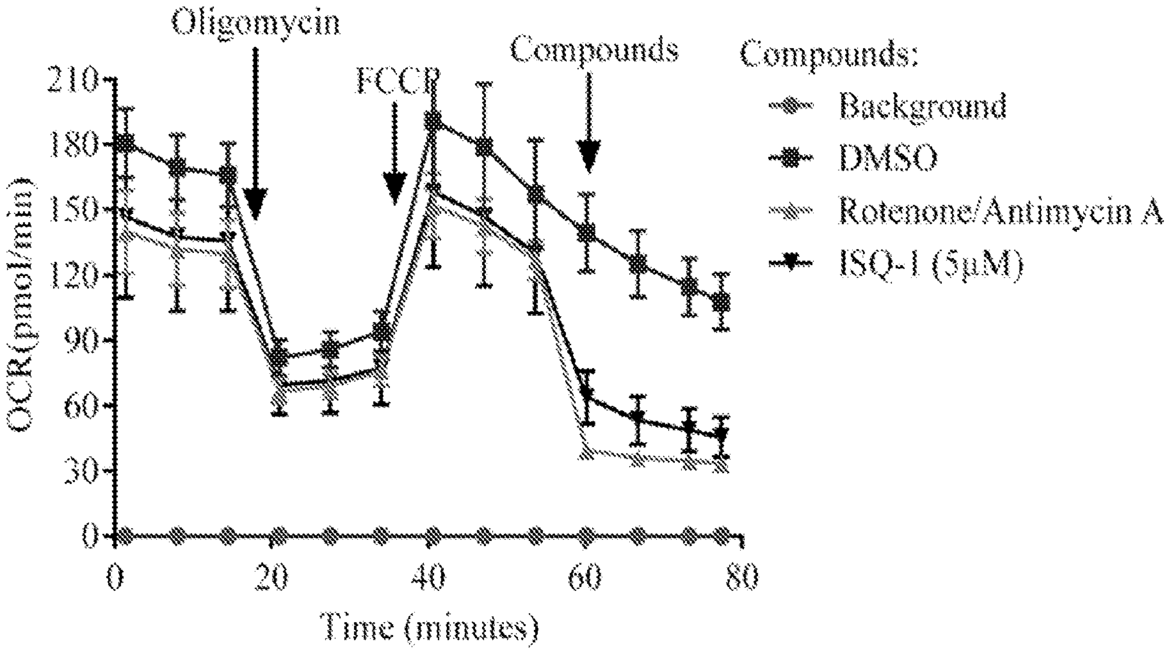
Figure 11:
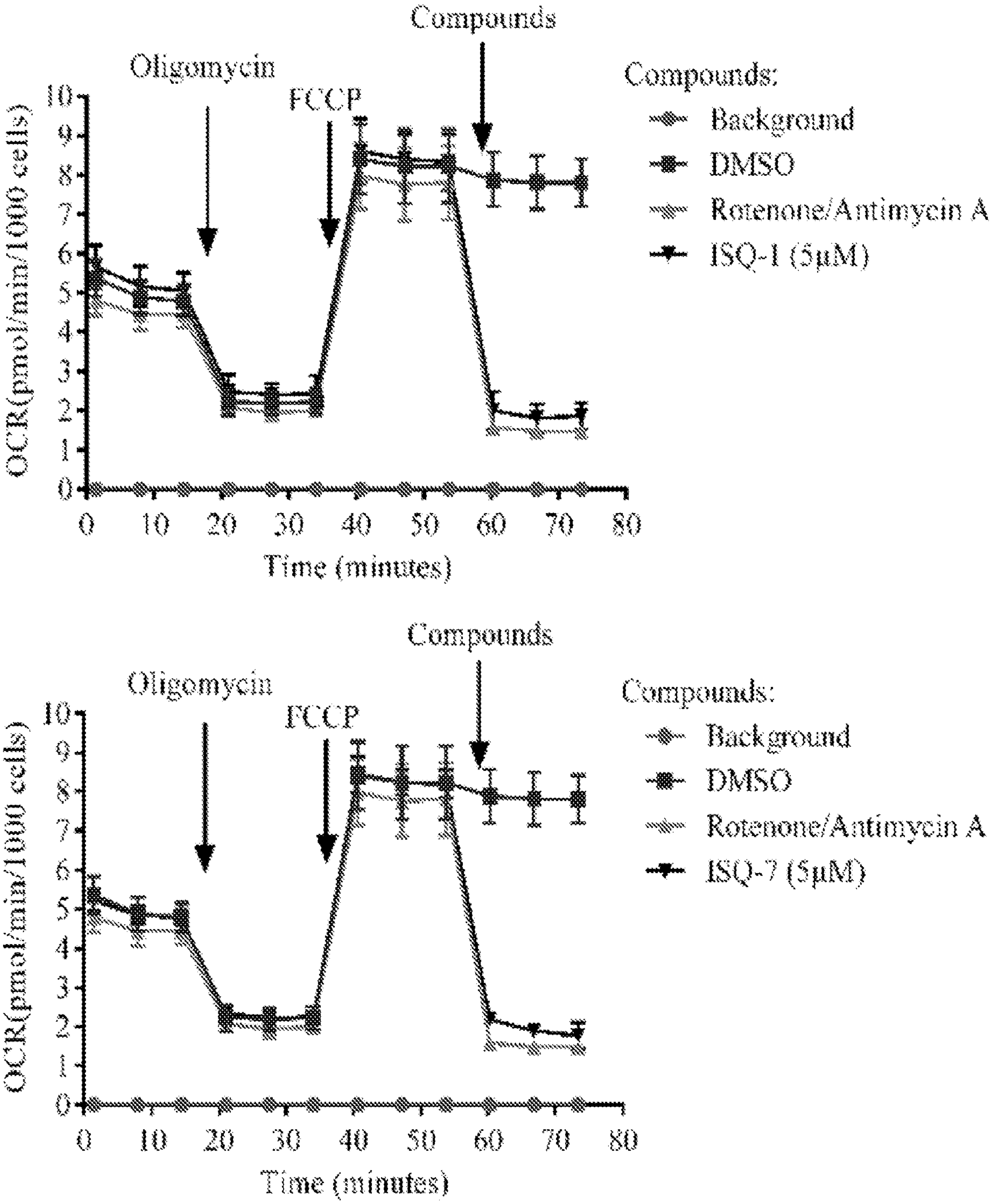
FIG. 11 shows graphs illustrating seahorse assay in Beas-2B cells. ETC complex complexes I/III inhibitors rotenone/antimycin were replaced with ISQ-1 (top), ISQ-7 (bottom), or DMSO. ISQ-1 and ISQ-7 showed similar inhibitory effects on OCR compared with rotenone/antimycin, suggesting that ISQ-1 and ISQ-7 inhibited ETC complex I or III.

Next, it was determined if ISQ-1 inhibited protein complexes in the electron transport chain (ETC). The effects of oligomycin, a known mitochondrial complex V/ATP synthase inhibitor, were compared with ISQ-1 in DMSO or with vehicle alone. As expected, oligomycin suppressed ATP-linked respiration and decreased OCR followed by an increased OCR upon the addition of FCCP that collapsed the inner membrane gradient and drove the ETC to function to its maximal rate (FIGS. 3B and 10). In contrast, in the presence of ISQ-1, the decreased OCR could not be "rescued" by the addition of FCCP (FIGS. 3B and 10), an outcome suggesting that ISQ-1 did not inhibit mitochondrial complex V. Antimycin A, a complex III inhibitor, and rotenone, a complex I inhibitor were next replaced with ISQ-1 in DMSO or vehicle alone in the Seahorse assay, which showed that ISQ-1 suppressed OCR to an extent that was similar to that of rotenone or antimycin (FIGS. 3C and 11). This implied that ISQ-1 inhibited either complex I or complex III of the ETC.

Figure 3D:
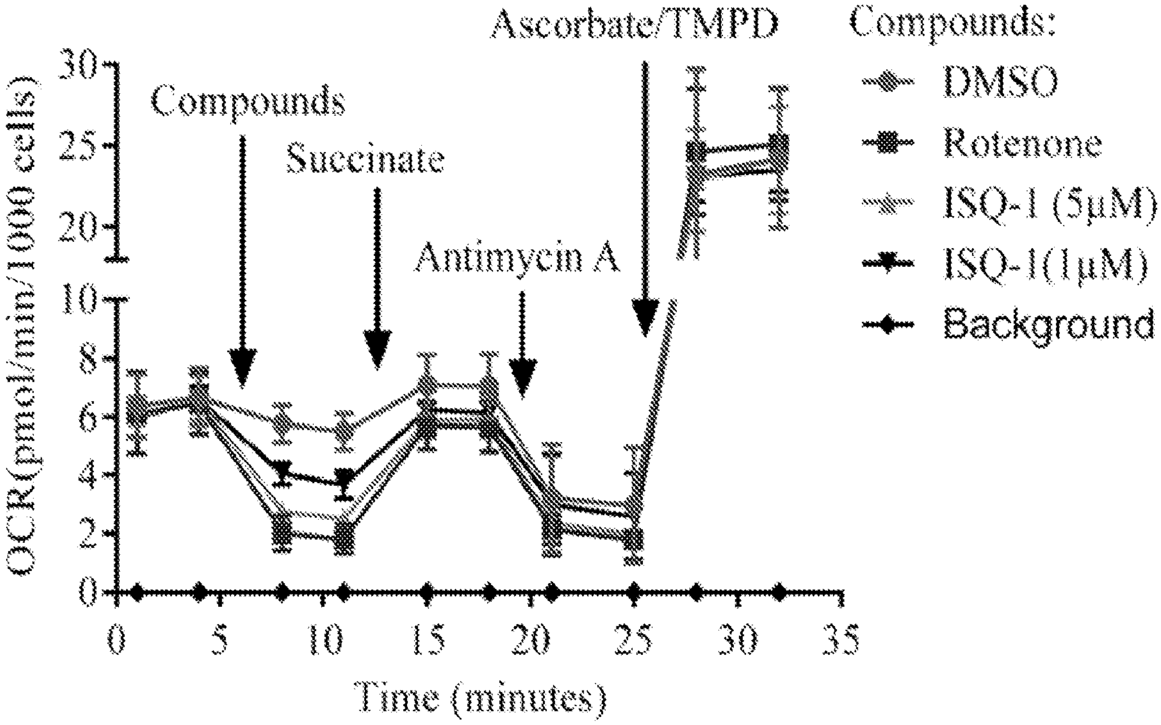
Figure 4A:
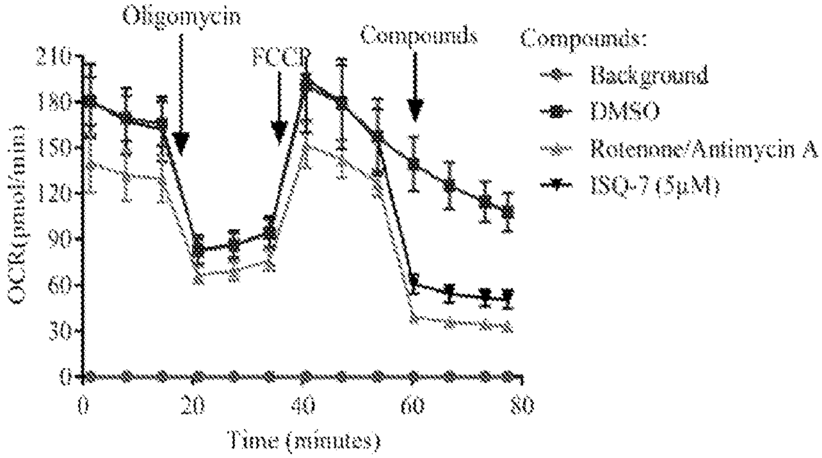
FIGS. 4A-D show graphs and images illustrating evaluation of a more potent ISQ analog ISQ-7. (A) Seahorse assay—ETC complex complexes I/III inhibitors rotenone/antimycin were replaced with ISQ-7 or DMSO. ISQ-7 showed similar inhibitory effects on OCR compared with rotenone/antimycin, suggesting that ISQ-1 inhibited ETC complex I or III. (B) Mitochondrial ETC complex activity measurements using PMP-permeabilized cells. PMP selectively disrupted cell membrane but left mitochondrial membrane intact. Similar to rotenone, ISQ-7 decreased OCR and this OCR inhibition was bypassed after addition of the complex II substrate succinate, suggesting that ISQ-7 inhibited ETC complex I. (C) ISQ-7 inhibited Wnt target genes c-Myc and Axin2 in a dose-dependent manner in LS174T cells after 24 hours treatment. (D) ISQ-7 activated AMPK and increased phosphorylation of AMPK target ACC in LS174T cells.
Figure 4B:
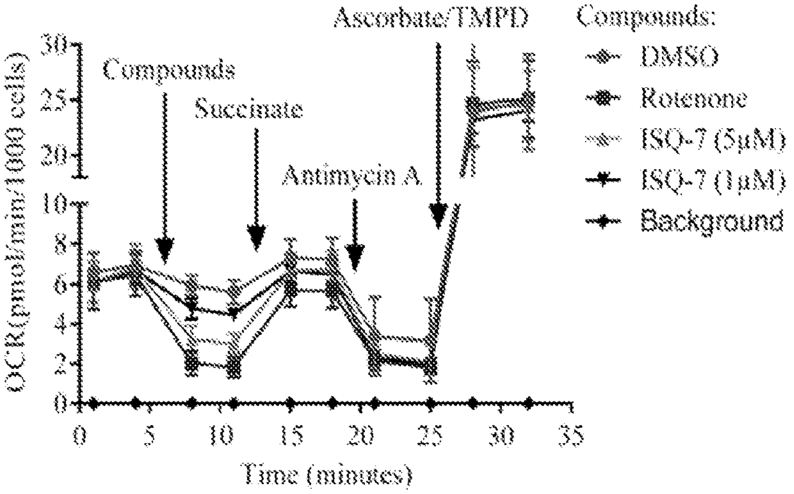
Figure 4C:
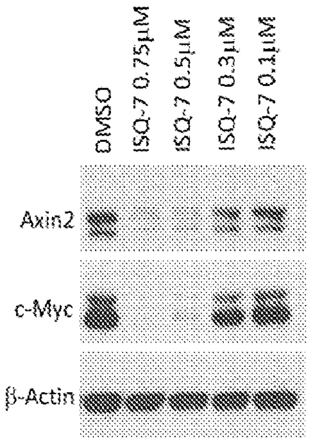
Figure 4D:
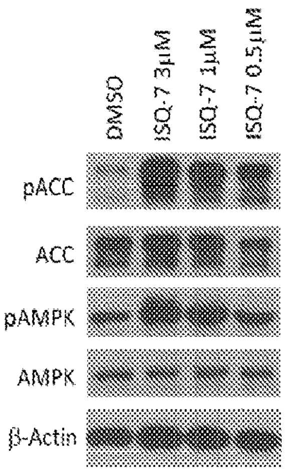

To reveal the precise mechanism by which ISQ-1 affected mitochondria, substrate specific ETC/oxidative phosphorylation activity was measured with or without the addition of ISQ-1 or known ETC complex inhibitors using plasma membrane permeabilizer (PMP)-treated cells. PMP is a bacterial recombinant cholesterol-dependent cytolysin that forms pores on plasma membranes while sparing mitochondrial membranes. These pores on plasma membranes facilitate the passage of solutes and small proteins and thereby allow the control of ETC complex-specific substrate/inhibitor provision. Permeabilized cells were given pyruvate, a complex I-linked substrate, followed by the addition of DMSO, and either the complex I inhibitor, rotenone, or ISQ-1. Surprisingly, it was noted that ISQ-1 halted pyruvate/NADH-linked respiration in a dose-dependent manner relative to DMSO alone (FIG. 3D). This effect was mimicked by the complex I inhibitor, rotenone, to a similar degree, and this outcome suggested that ISQ-1 was a complex I inhibitor. Next, succinate was added to drive respiration from electrons that were fed directly into the ubiquinone pool by succinate dehydrogenase (complex II) that by-passed complex I inhibition. Both rotenone-treated and ISQ-1-treated permeabilized cells showed increased respiration (FIG. 3D), an outcome that ruled out the possibility that ISQ-1 inhibited complexes II, III, or IV. As anticipated, the subsequent addition of complex III inhibitor, antimycin A, abolished OCR but this abolition was "rescued" by the injection of a complex III electron donor, N,N,N,N-tetramethyl-p-phenylenediamine (TMPD) (FIG. 3D), essentially by-passing the blockade at complex III and delivering electrons directly to cytochrome c oxidase (complex IV). In summary, the Seahorse assay data using ETC complex-specific inhibitors and PMP-permeabilized cells demonstrated that ISQ-1 inhibited complex I, disrupted mitochondrial function, activated AMPK, and inhibited Wnt signaling. Similar results were obtained for ISQ-7, a more potent analog of ISQ-1 (FIGS. 2A-B). Seahorse assays showed that ISQ-7 inhibited complex I or III (FIGS. 4A and 11) and mitochondrial ETC complex activity measurements on permeabilized cells by PMP further revealed that ISQ-7 inhibited complex I (FIG. 4B). In a fashion similar to ISQ-1, ISQ-7 strongly inhibited Wnt target genes, Axin-2 and c-Myc (FIG. 4C) and activated AMPK (FIG. 4D) in a dose-dependent manner.

Figure 5A:
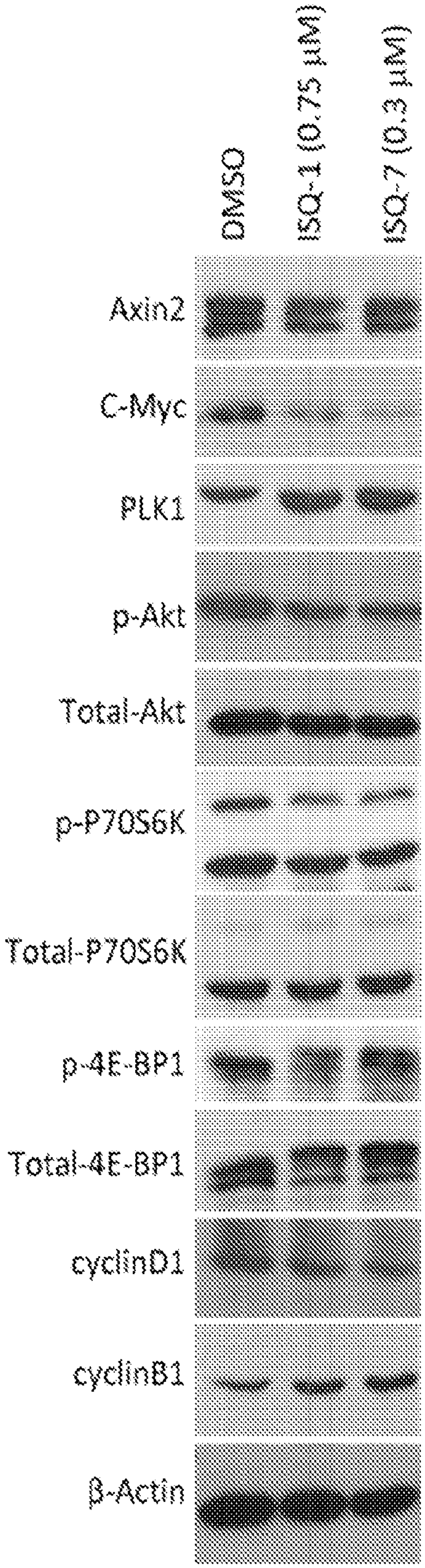
FIGS. 5A-D show images illustrating combinational effects of ISQs and Plk1 inhibitors on c-Myc expression after 24 hours treatment. (A) Effects of ISQ-1 and ISQ-7 on cell signaling pathways in LS174T colon cells with and without a cell cycle regulator Plk1. A key cell cycle regulator Plk1 was induced upon drug treatment. (B) Combination of ISQ-1 or ISQ-7 with Plk1 inhibitor BI2536 resulted in enhanced depletion of c-Myc in LS174T cells. (C) Combination of ISQ-1 or ISQ-7 with Plk1 inhibitor GSK461364 resulted in enhanced depletion of c-Myc in LS174T cells. (D) Combination of ISQ-1 with Plk1 inhibitor B12536 resulted in enhanced depletion of c-Myc in prostate cancer PC3 cells.
Figure 5B:
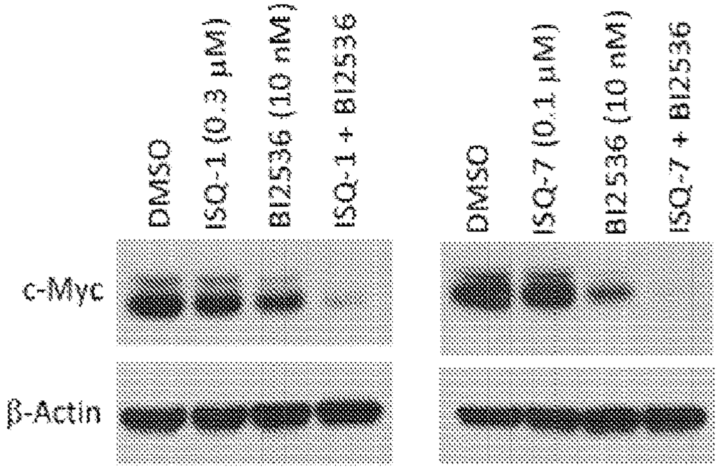

To understand the mechanisms of ISQs and to identify other drugs with potential lethal effects in combination with ISQs, the effects on ISQs on several cell signaling pathways were analyzed (FIG. 5A). Perhaps not unexpectedly, these compounds inhibited the expression and activation of Wnt and mTOR signaling and affected cell cycle progression, consistent with their function as mitochondrial complex I inhibitors that altered ATP levels. Surprisingly, however, it was found that a key cell cycle regulator, Plk1, was upregulated by ISQs (FIG. 5A). Plk1, a well-known oncoprotein, is highly overexpressed in human colorectal tumors compared with adjacent normal tissues. Plk1 is required for cell cycle progression and its expression is associated with drug resistance. More importantly, Plk1 promoted the phosphorylation of c-Myc at serine-62 that enhanced c-Myc stability in colorectal cancer and breast cancer, and Plk1 inhibitor BI2536 suppressed this oncogenic c-Myc stabilization. Because ISQs reduced c-Myc levels through inhibiting Wnt signaling, it was explored whether ISQs possessed synergistic effects with BI2536 with respect to c-Myc levels. Co-treatment of LS174T cells with the combination of either ISQ-1 or ISQ-7 and with BI2536 for 24 hours led to synergistic reduction of c-Myc levels compared with the effects of either ISQ-1 or ISQ-7 when used alone (FIG. 5B).

Figure 5C:
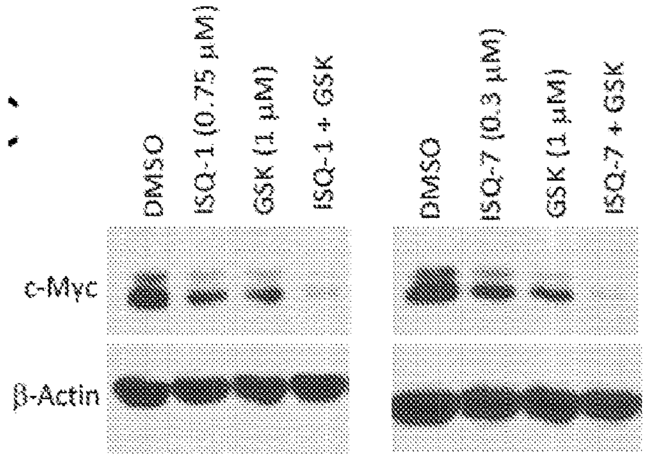
Figure 5D:
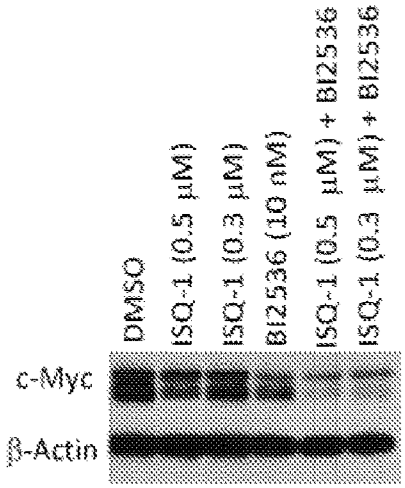
Figure 6A:
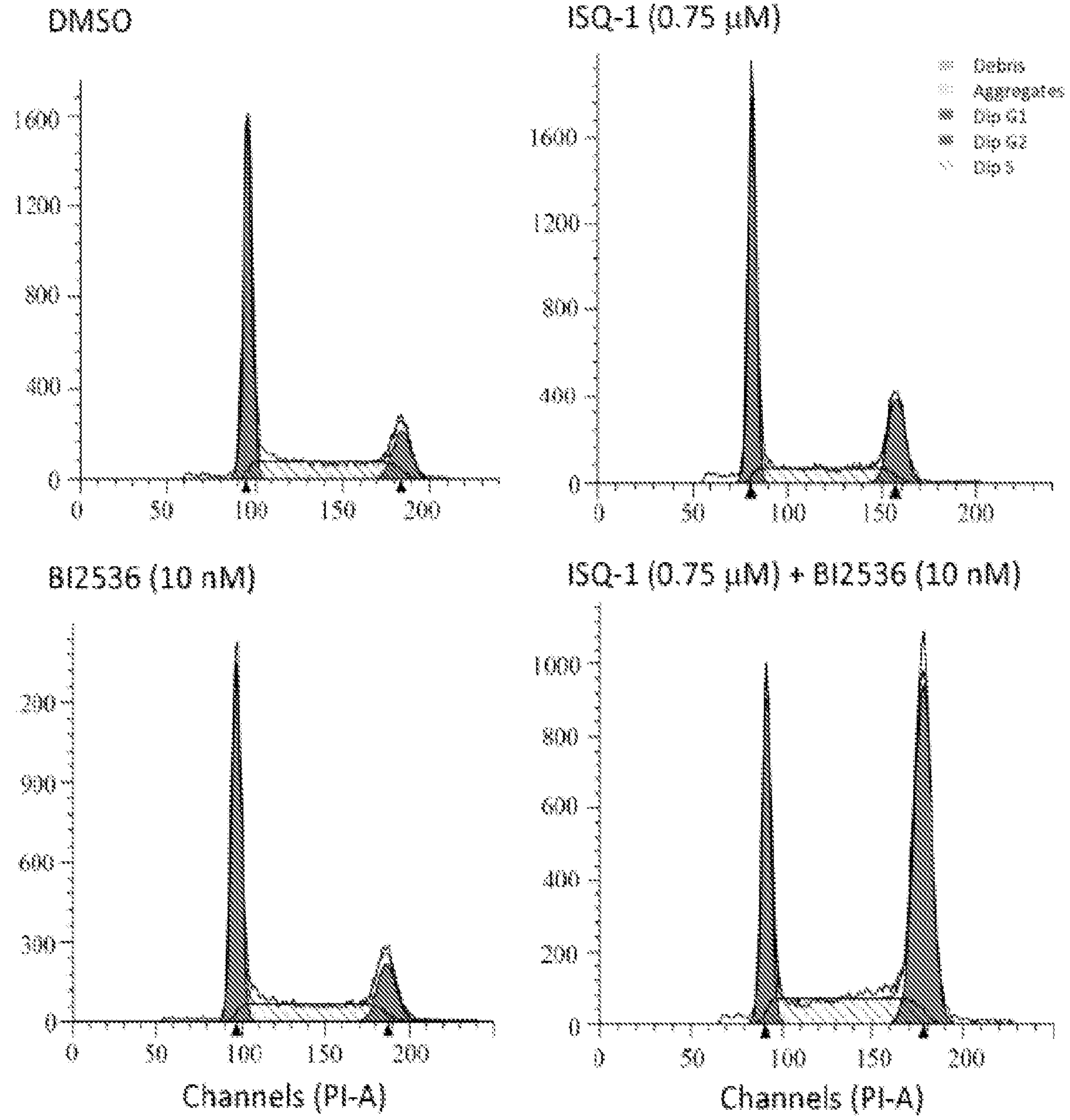
FIGS. 6A-B show graphs and images illustrating synergistic effects of ISQ-1 and B12536 on colon cancer cell proliferation. (A) ISQ-1 and BI2536 collectively inhibited cell cycle progression of LS174T colon cancer cells after 24 hours treatment. (B) ISQ-1 and BI2536 synergistically inhibited the proliferation of LS174T cells. Synergy scores were determined using SynergyFinder with Bliss as a reference model.
Figure 6B:
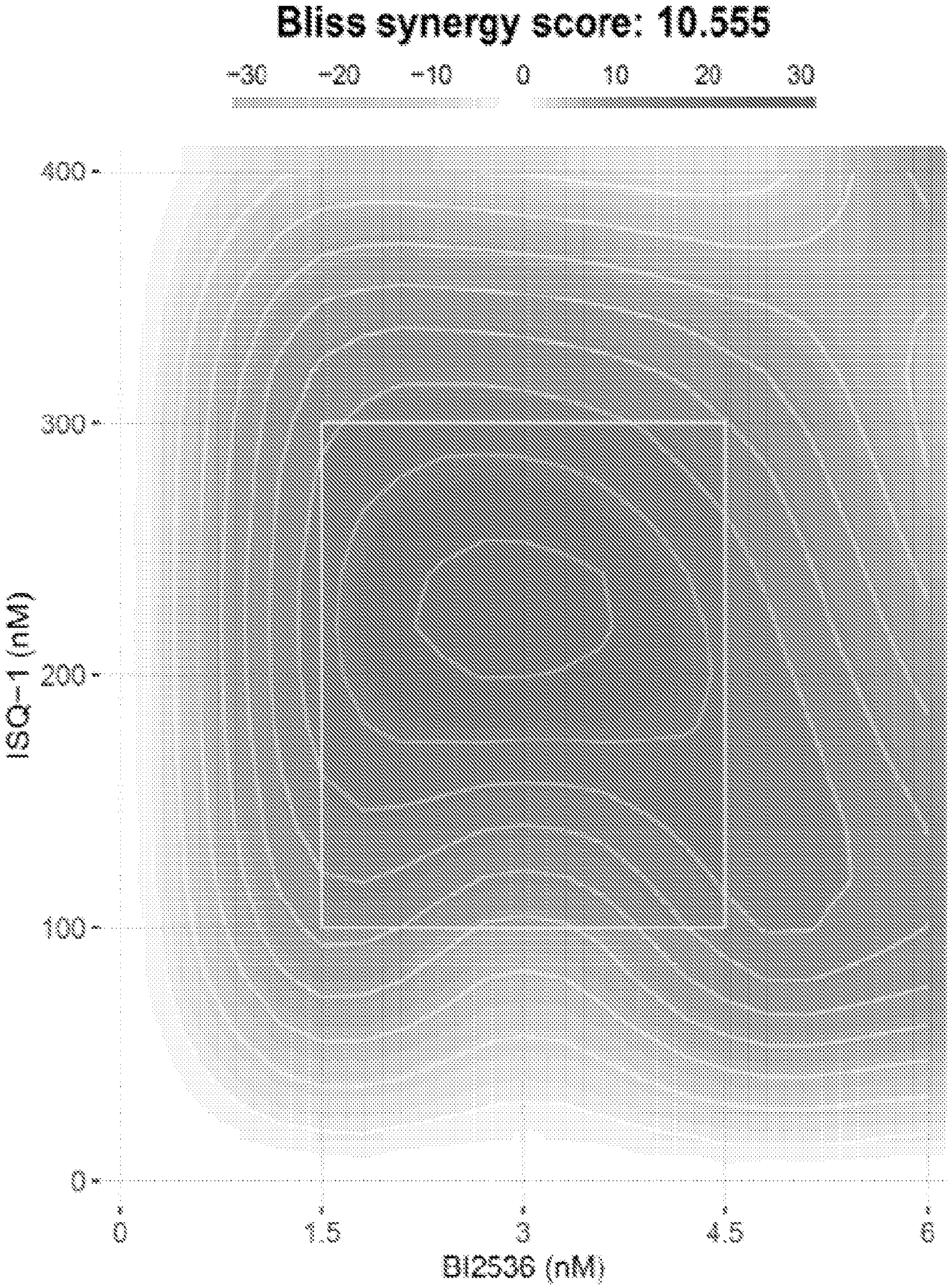

To validate these results, this experiment was repeated with another well-characterized Plk1 inhibitor, GSK461364, that has been approved for clinical trials. Similar to BI2536, GSK461364 synergized with ISQ-1 or ISQ-7 on c-Myc inhibition (FIG. 5C). Similar results were obtained in prostate cancer PC3 cells (FIG. 5D). The effects of ISQ-1 and BI2536 on cell cycle of LS174T colorectal cancer cells were also analyzed. The combination of these two compounds synergistically inhibited the G2/M transition (FIG. 6A). To confirm that the relationship between ISQ-1 and BI2536 was synergistic rather than additive, synergy scores were calculated using SynergyFinder web application (Version 2.0) at default parameters with Bliss as the reference model. It was found that the average synergy score was >10 and at certain concentrations (ISQ-1 100-300 nM and BI2536 1.5-4.5 nM) the corresponding synergy score was >15 (FIG. 6B), indicating that ISQ-1 indeed synergized with BI2536. Collectively, these data provided a rationale for further evaluation of ISQs in combination with Plk1 inhibitors.

Figure 7A:
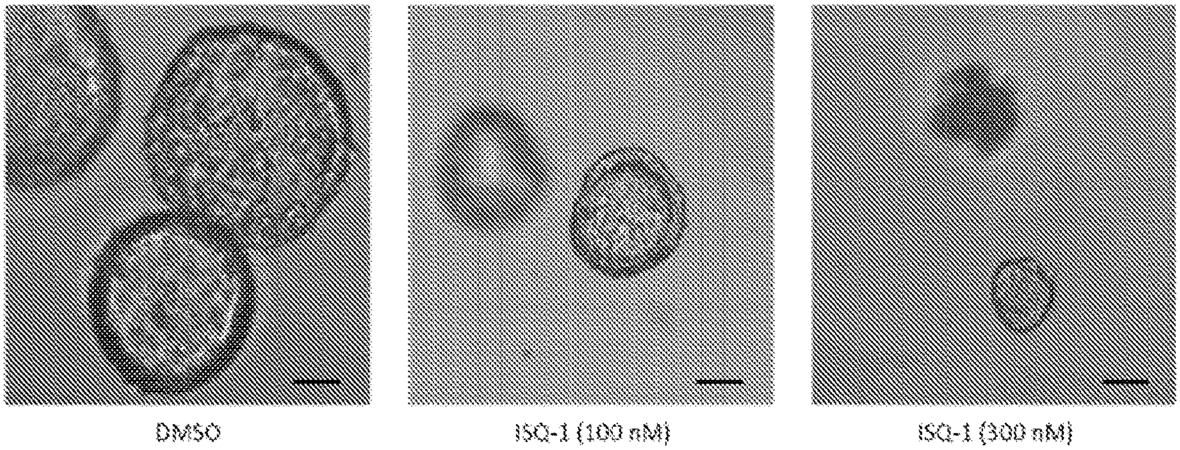
FIGS. 7A-C show images and graphs illustrating ISQ-1 inhibited mouse colon cancer organoids from $Apc^{fl/+}$/$Kras^{LSL-G12D}$/Villin-Cre mouse model. (A) Colony formation of colon cancer organoids from single cells after DMSO or ISQ-1 treatment at day 7. Scale bar, 50 μm. (B) ISQ-1 inhibited organoid colony formation. Total number of organoids formed from single cells in the presence of DMSO or ISQ-1 at day 7 was quantified. (C) ISQ-1 inhibited organoid growth after 3-day treatment. ISQ-1 or DMSO were added after organoids were formed from single cells. Organoid viability was measured using CellTiter-Glo® 3D Cell Viability Assay (Promega).
Figure 7B:
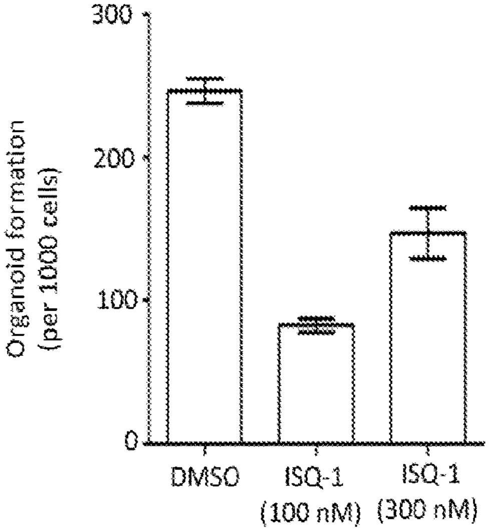
Figure 7C:
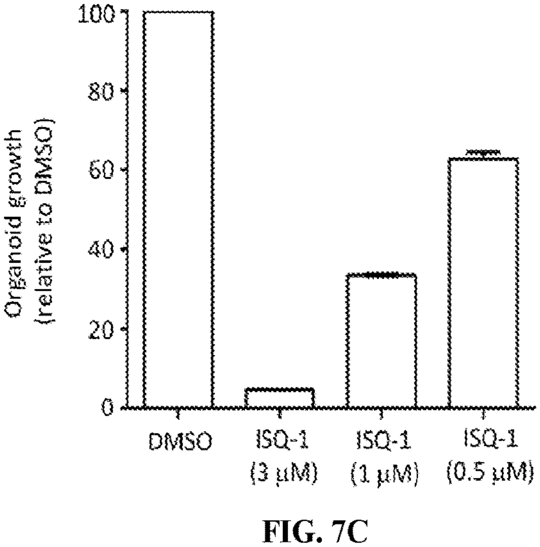
Figure 8A:
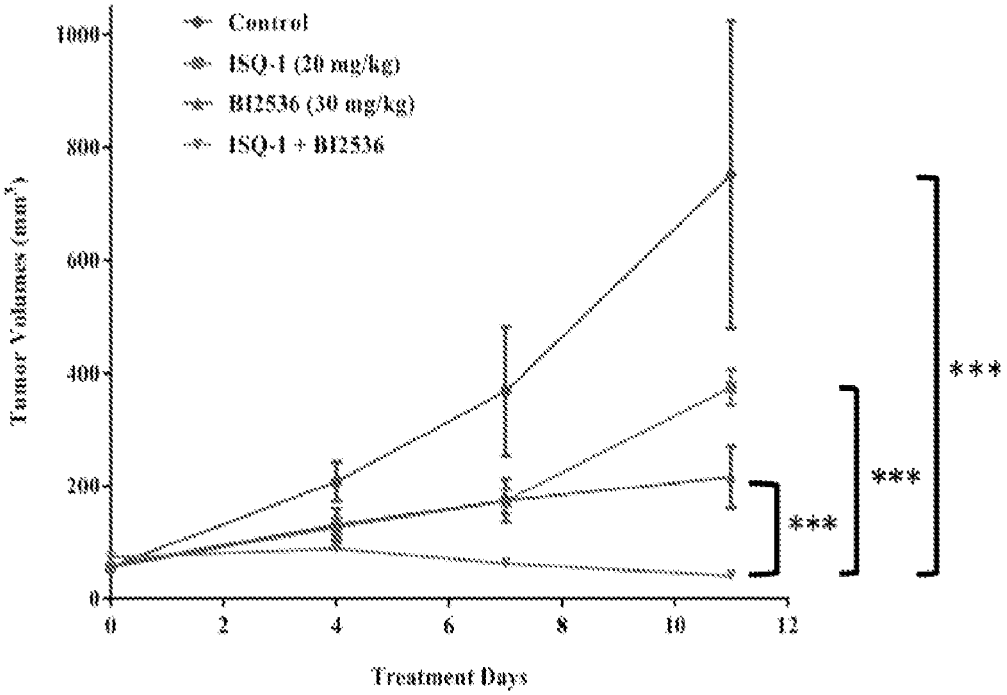
FIGS. 8A-E show graphs and images illustrating that ISQ-1 and the Plk1 inhibitor BI2536 synergistically inhibited colon cancer cell xenografts in vivo. (A and B) ISQ-1 (20 mg/kg/day) and B12536 (30 mg/kg twice a week) synergistically induced regression of LS174T colon cancer cell xenografts in nude mice. ***$P<0.001$, analysis of variance (ANOVA) followed by Tukey's HSD test. (C) Mouse weight measurements following various treatments. (D) H&E staining of tumors (a: control; b: ISQ-1; c: B12536; d: ISQ-1+BI2536). (E) ISQ-1 and B12536 collectively inhibited Ki-67 expression in LS174T xenografted tumors (a: control; b: ISQ-1; c: B12536; d: ISQ-1+BI2536).
Figure 8B:
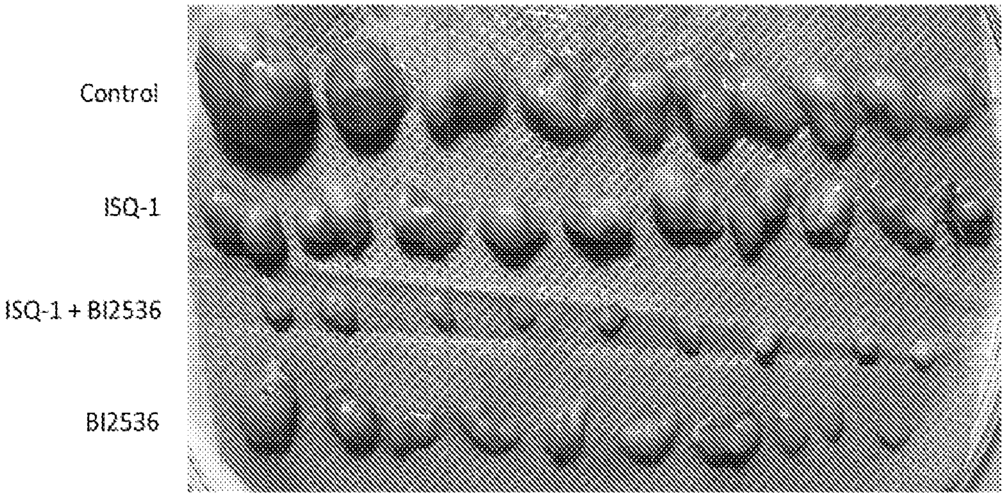
Figure 8C:
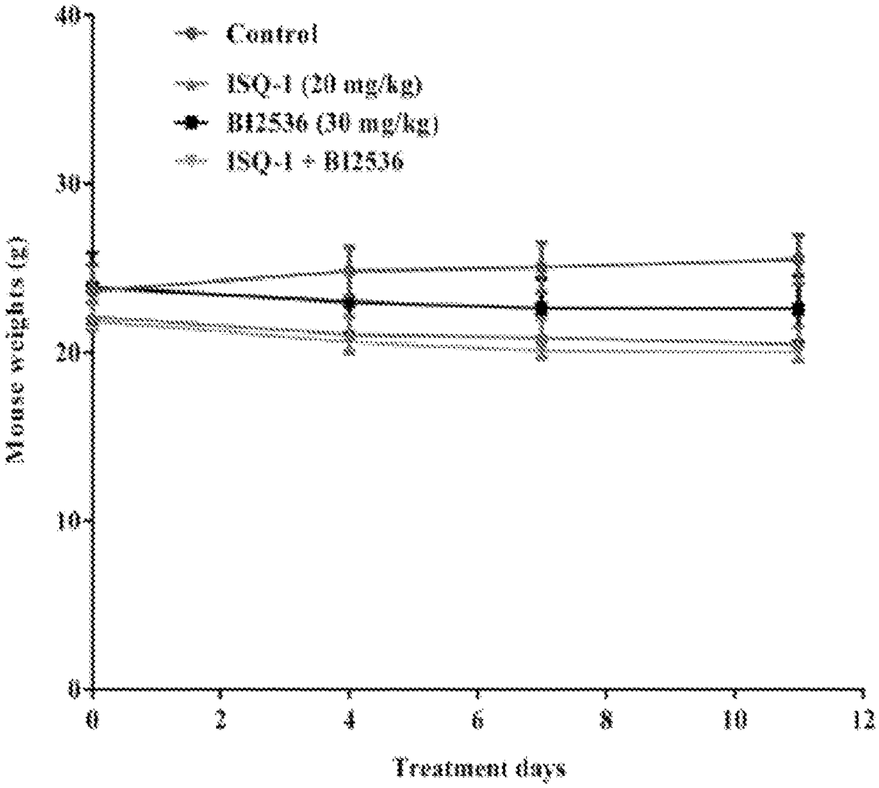
Figure 8D:
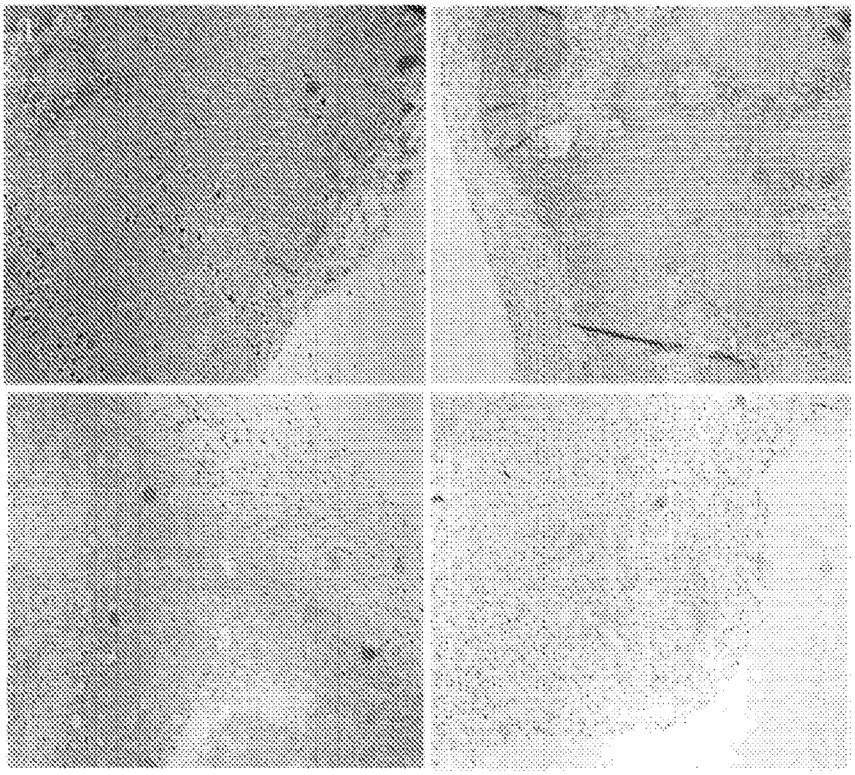
Figure 8E:
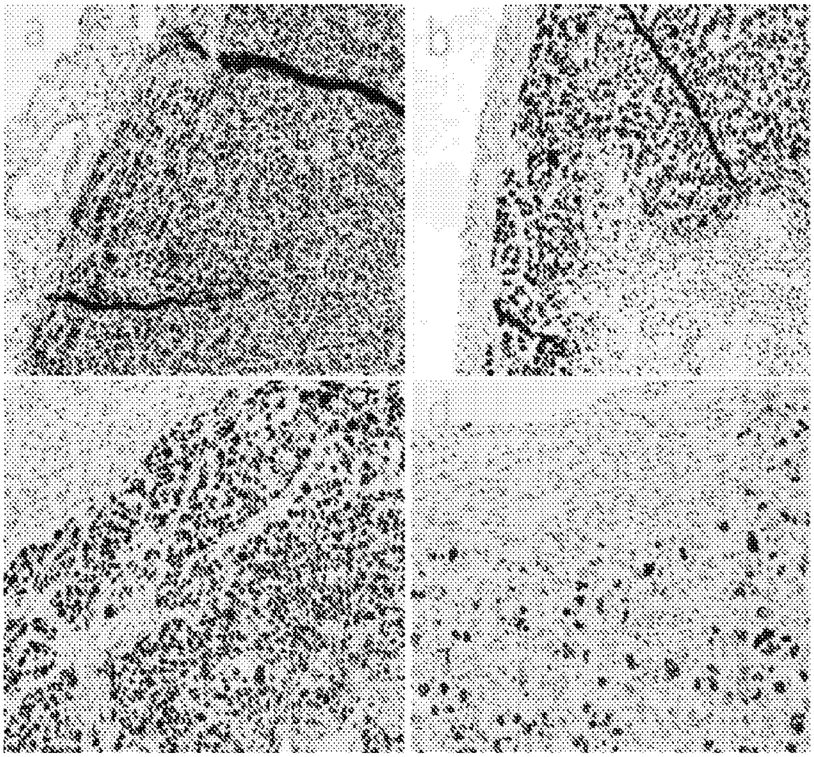

Although ISQ-1 was less potent than ISQ-7 in vitro, its solubility was better than that of ISQ-7. ISQ-1 was evaluated using a more pathologically relevant, 3D-tumor organoid model established from $Apc^{fl/+}$/$Kras^{LSL\text{-}G12D}$/Vil-Cre compound mutant mouse. ISQ-1 inhibited tumor organoid formation from single cells (FIGS. 7A-B) and inhibited organoid growth in a dose-dependent manner (FIG. 7C), a finding that prompted the present inventors to explore the in vivo therapeutic efficiencies of ISQ-1 and its combination with a Plk-1 inhibitor. A colon cancer xenograft model established from LS174T cells in nude mice was used to assess the in vivo tumor inhibitory potential of the ISQ-1 and Plk1 inhibitor BI2536. Daily dosing of ISQ-1 at 20 mg/kg body weight daily or BI2536 at 30 mg/kg body weight twice a week inhibited tumor growth but did not induce tumor regression (FIGS. 8A-B). The combination therapy of ISQ-1 and BI2536 resulted in significant tumor remission (FIGS. 8A-B) relative to either compound used alone. No gross toxicities were observed on the basis of mouse weight measurements (FIG. 8C). Tumor sections were analyzed with H&E and Ki-67 staining (FIGS. 8D-E). The tumors displayed poorly differentiated carcinomas with pleomorphism and brisk mitotic activity. The tumors treated with a combination of ISQ-1 and BI2536 were more pleomorphic (i.e., large nuclei, prominent nucleoli, considerable variation in nuclear size, etc.) than that those treated with individual compounds (FIG. 8E). The combination treatment with ISQ-1 and B12536 was more effective in inhibiting tumor proliferation (FIG. 8E) than either agent alone.

Discussion

Figure 12:
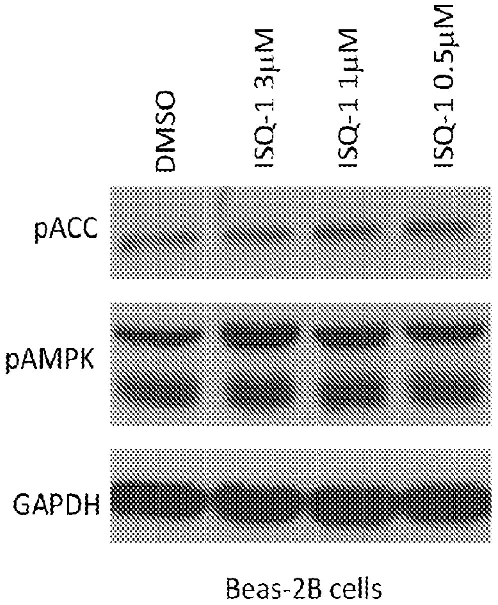
FIG. 12 shows an image illustrating the effects of ISQ-1 on AMPK signaling in Beas-2B cells. ISQ-1 was less effective in activating AMPK signaling in Beas-2B cells compared with it activity in CRC cells (FIG. 1E).

Building on their long-standing efforts to identify and develop potential drug candidates for cancer treatment, the present inventors discovered Wnt signaling inhibitors featuring an indole-substituted, quinoline scaffold called ISQs. A representative compound, namely ISQ-1 (FIG. 2A), possessed nanomolar potencies towards inhibiting Wnt signaling and cell proliferation in multiple tumor cell lines. A series of Agilent Seahorse assays and mitochondrial ETC complex activity measurements using PMP-permeabilized cells revealed that ISQ-1 and ISQ-7 were not mitochondrial proton uncouplers but rather mitochondrial ETC complex I inhibitors. Mechanistically, ISQs inhibited mitochondrial complex I, disrupted mitochondrial respiration function, reduced energy supply for signaling transduction, and thus inhibited aberrantly active Wnt-o-catenin signaling that contributed to cell proliferation in more than 90% of colorectal cancers. Recent studies indicated that a majority of tumor cells, particularly cancer stem cells, depended on oxidative phosphorylation for ATP production. In comparison with normal cells, colorectal cancers often harbor tumor-specific, nonsynonymous mutations or copy-number alterations in mitochondrial DNA (mtDNA) that render them more sensitive to less potent complex I inhibitors and that also confer ISQs selectivity toward colorectal cancer cells over healthy cells. Although ISQ-1 also inhibited mitochondrial oxidative phosphorylation in normal epithelial cells (Beas-2B) (FIGS. 9-11), it was less active in activating AMPK signaling in normal cells (FIG. 12) than it was in cancer cells (FIG. 2E), an observation that confirmed selectivity of ISQs for cancer cells over normal cells.

A growing body of evidence connects mitochondrial oxidative phosphorylation with drug resistance in multiple cancer types. A subset of diffuse, large B cell lymphoma cells escaped from inhibition of B cell receptor (BCR) survival signals and persisted because of enhanced mitochondrial function. Increased mitochondrial metabolism through Pgc1α/c-Myc-mediated transcriptional regulation pathways also played a role in exacerbated growth and chemotherapy resistance in melanoma and in triple-negative breast cancer. Mutations in the subunit gene, Smarca4, of the SWI/SNF chromatin remodeling complex led to dependence of Smarca4-deficient lung tumors on elevated oxidative phosphorylation. Kinase inhibitors, such the EGFR inhibitor, gefitinib, and the BRAF V600E inhibitor, vemurafenib, induced enhanced mitochondrial metabolism and drug resistance. These drug-resistance cases highlight the potential use of ISQs for targeting oxidative phosphorylation as a therapeutic opportunity in multiple well-defined refractory cancers and provides an approach for overcoming certain types of drug resistance.

Figure 13:
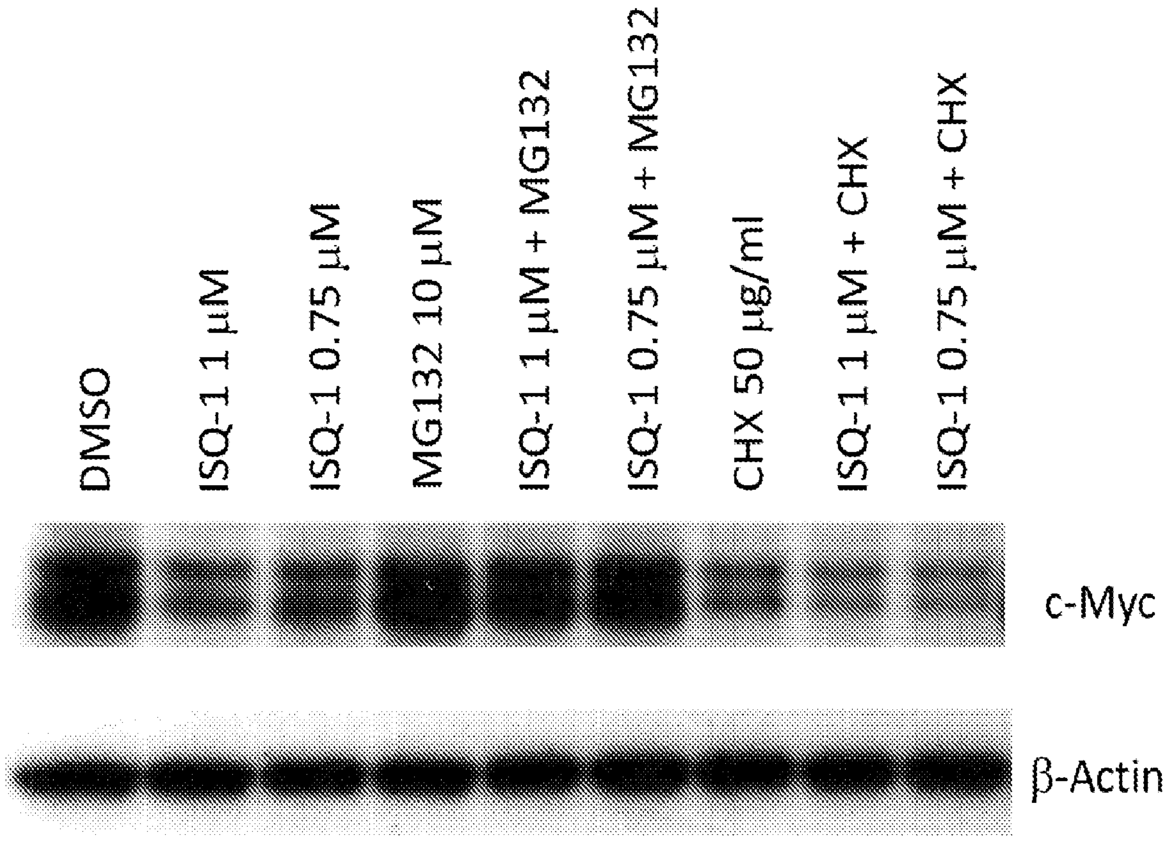
FIG. 13 shows an image illustrating the effects of ISQ on protein levels of c-Myc in CRC cells. ISQ-1 treatment reduced c-Myc in LS174T cells and this reduction was blocked by proteasome inhibitor MG132 and enhanced by protein translation inhibitor cycloheximide (CHX). LS174T cells were treated by ISQ-1 at indicated concentrations for 24 hours followed by MG132 treatment (10 μM, 6 hours) or CHX (50 μg/mL, 2 hours).

MYC, a master regulator of cell cycle and proliferative glycolysis, is a well-established Wnt signaling target gene, and the encoded MYC proteins present formidable challenges for pharmacological targeting. This Example shows that ISQs decrease c-Myc protein levels in colon cancer cell line LS174T. This c-Myc reduction was accompanied by unexpected increase of Plk1 (FIG. 5A), another positive cell cycle regulator. In neural cancers, Plk1 indirectly increased n-Myc by phosphorylating SCF-Fbw7 E3 ubiquitin ligase and inducing its proteasomal degradation that counteracted SCF-Fbw7-mediated degradation of n-Myc. In colorectal cancer and breast cancer, Plk1 promoted the phosphorylation of c-Myc at serine-62 that enhanced c-Myc stability. ISQ-1 treatment reduced c-Myc in LS174T cells, and this effect was blocked by proteasome inhibitor MG132 and enhanced by protein translation inhibitor cycloheximide (CHX) (FIG. 13), outcomes that suggested that ISQ-1 regulated c-Myc at multiple levels. It was observed in this Example that ISQ-1 induced both Plk-1 and cyclin B1 in colon cancer cells (FIG. 5A). Cooperation of Plk1 and Cyclin B1 plays an essential role in G2/M transition that may lead to resistance to ISQs treatment. Based on these data, the present inventors developed a combination therapy of ISQs and Plk1 inhibitor BI2536 which achieved remarkable synergistic reduction of c-MYC expression and cell cycle progression in vitro and tumor remission in vivo.

Although BI2536 proved to be safe in phase I clinical trials, it displayed only limited antitumor activity in Phase II clinical trials. ISQ-1 significantly enhanced the efficacies of BI2536 both in vitro (FIGS. 6A-B) and in vivo (FIGS. 8A-E) and suggested that ISQs and Plk1 inhibitors could provide effective combinational therapies. In this Example, the present inventors focused on c-Myc regulation by ISQs and Plk1 inhibitors. However, these inhibitors may have synergistic effects on other cancer targets as well. In addition, ISQs may also enhance the efficacy of the other therapeutic agents. For example, cancer immunotherapy has revolutionized cancer treatment and a small portion of patients show complete tumor remission after immune checkpoint blockade therapies. MYC has been shown to regulate immune checkpoint molecule PD-L1 and cooperates with Ras to induce an immune suppressive tumor microenvironment to drive tumorigenesis. Recently, a small molecule MYC inhibitor, called MYCi361, induced immunogenic cell death (ICD), modulated antitumor tumor immune microenvironment, and synergized with immune checkpoint blockade therapy. Without wishing to be bound by theory, it is believed that the newly identified ISQs disclosed herein, in combination with Plk1 inhibition, would not only support an effective combination approach of pharmacological targeting c-Myc driven cancers but also highlight the potential of synergizing with immune checkpoint blockade therapies to eradicate refractory "MYC-addicted" cancers.

Materials and Methods

Chemistry

General Methods.

Solvents and chemicals were used from commercial vendors without further purification unless otherwise noted. A published procedure (30) for the synthesis of substituted quinolines was used for the synthesis of ISQs. The synthesis of indole-substituted quinolines (ISQs) utilized 4-(N,N-dialkylamino-2-aminobenzaldehydes prepared by sequential nucleophilic aromatic substitution reactions of 4-fluoro-2-nitrobenzaldehyde with secondary amines and the subsequent reduction of the intermediate 4-dialkylamino-2-nitrobenzaldehydes with iron powder. A Friedlander condensation of these 4-(N,N-dialkylamino-2-aminobenzaldehydes with 2-(1-methyl-1H-indol-3-yl)acetonitrile, as described previously (30), secured the desired ISQs (FIG. 1A).

Nuclear magnetic resonance spectra were determined in dimethyl sulfoxide-$d_6$ (DMSO-$d_6$) using Varian instruments ($^1H$, 400; $^{13}C$, 100 Mz). High resolution electrospray ionization (ESI) mass spectra were recorded using a LTQ-Orbitrap Velos mass spectrometer (Thermo Fisher Scientific, Waltham, MA, USA). The FT resolution was set at 100,000 (at 400 m/z). Samples were introduced through direct infusion using a syringe pump with a flow rate of 5 μL/min. Melting points were determined in open capillarity tubes with a Buchi B-535 apparatus and are uncorrected. Purity was established by combustion analyses performed by Atlantic Microlabs, Inc. (Norcross, GA).

$N^7$,$N^7$-Dimethyl-3-(1-methyl-1H-indol-3-yl)quinoline-2,7-diamine (ISQ-1)

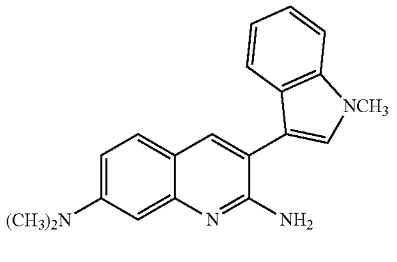

Purified by recrystallization from acetonitrile: Yield 45%, mp 152-155° C. $^1H$ NMR, 400 MHz (DMSO-$d_6$): δ ppm 7.76 (s, 1H), 7.58 (s, 1H), 7.55 (d, J=7.6, 1H), 7.52 (d, J=8 Hz, 1H, 7.5 (d, J=8.4 Hz, 1H), 7.23 (t, J=8 Hz, 1H), 7.1 (t, J=8 Hz, 1H), 6.86 (dd, J=8.8 Hz and 2.4 Hz, 1H), 6.65 (d, J=2.4 Hz, 1H), 5.84 (s, 2H), 3 (s, 6H). $^{13}C$ NMR, 100 MHz (DMSO-$d_6$): δ ppm 156.6, 151, 148, 136.8, 135.7, 128.7, 127.8, 126.5, 121.6, 119.4, 119.3, 115.8, 113.4, 111, 110.5, 110.1, 103.9, 40.3, 32.6. HRMS (ESI) Calcd for $C_{20}H_{21}N_4$ [$MH^+$]: 317.1761. Found: 317.1748. Anal. Calcd for $C_{20}H_{20}N_4$: C, 75.92; H, 6.37. Found: C, 75.77; H, 6.26.

3-(1-Methyl-1H-indol-3-yl)-7-(piperidin-1-yl)quinolin-2-amine (ISQ-2)

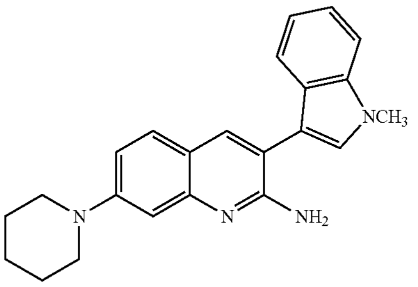 [SMILES: Cn1cc(-c2cc3ccc(N4CCCCC4)cc3nc2N)c2ccccc21]

Purified by recrystallization from acetonitrile: Yield 48%, mp 175-177° C. $^1H$ NMR, 400 MHz (DMSO-$d_6$): δ ppm 7.77 (s, 1H), 7.58 (s, 1H), 7.49-7.57 (m, 3H), 7.24 (dt, J=8 Hz and 0.8 Hz, 1H), 7.1 (dt, J=8 Hz and 0.8 Hz, 1H), 7 (dd, J=8.8 Hz and 2.4 Hz, 1H), 6.83 (d, J=2.4 Hz, 1H), 5.82 (s, 2H), 3.86 (s, 3H), 3.25 (t, J=5.2 Hz, 4H), 1.57-1.68 (m, 6H). $^{13}C$ NMR, 100 MHz (DMSO-$d_6$): δ ppm 156.7, 152.1, 148.1, 136.8, 135.4, 128.8, 127.6, 126.5, 121.7, 119.4, 119.3, 117.1, 114.3, 114.2, 110.5, 110.2, 107.4, 49.5, 32.6, 25.2, 24.1. HRMS (ESI) Calcd for $C_{23}H_{25}N_4$ [$MH^+$]: 357.2074. Found: 357.2077. Anal. Calcd for $C_{23}H_{24}N_4$: C, 77.50; H, 6.79. Found: C, 77.30; H, 6.95.

3-(1-Methyl-1H-indol-3-yl)-7-(4-methylpiperazin-1-yl)quinolin-2-amine (ISQ-3)

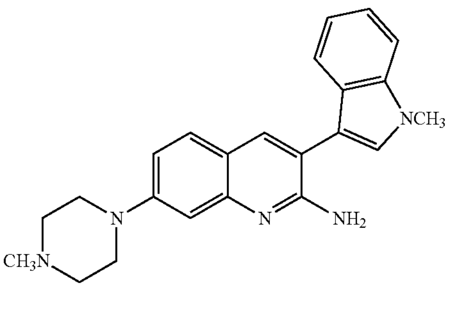

Purified by recrystallization from acetonitrile: Yield 24%, mp 188-190° C. $^1H$ N MR, 400 MHz (DMSO-$d_6$): δ ppm 7.78 (s, 1H), 7.59 (s, 1H), 7.51-7.56 (m, 3H), 7.24 (dt, J=8 Hz and 0.8 Hz, 1H), 7.1 (dt, J=8.4 Hz and 0.8 Hz, 1H), 7.01 (dd, J=9.2 Hz and 2.4 Hz, 1H), 6.88 (d, J=4.8 Hz, 4H), 5.85 (s, 2H), 3.85 (s, 3H), 3.24 (t, J=5.2 Hz, 4H), 2.48 (t, J=5.2 Hz, 4H), 2.24 (s, 3H). $^{13}C$ NMR, 100 MHz, (DMSO-$d_6$): δ ppm 156.7, 148, 136.8, 135.4, 128.8, 127.7, 126.5, 121.7, 119.5, 119.3, 117.3, 114.6, 113.6, 110.4, 110.1, 107.3, 54.6, 48.1, 45.8, 32.6. HRMS (ESI) Calcd for $C_{23}H_{26}N_5$[$MH^+$]: 372.2183. Found: 372.2188. Anal. Calcd for $C_{23}H_{25}N_5$: C, 74.36; H, 6.78. Found: C, 74.15; H, 6.70.

7-(4-Isopropylpiperidin-1-yl)-3-(1-methyl-1H-indol-3-yl)quinolin-2-amine. (ISQ-4)

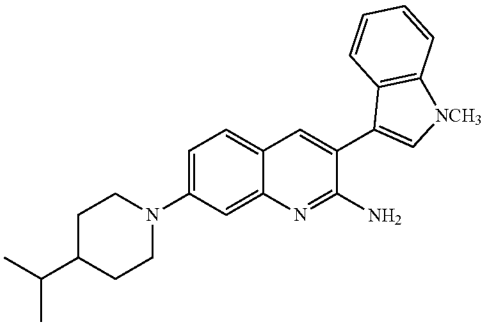 [SMILES: CC(C)C1CCN(c2ccc3cc(-c4cn(C)c5ccccc45)c(N)nc3c2)CC1]

Purified by recrystallization from acetonitrile: Yield 68%. $^1H$ NMR, 500 MHz (DMSO-$d_6$): δ ppm 7.77 (s, 1H), 7.59 (s, 1H), 7.49-7.55 (m, 3H), 7.24 (t, J=7 Hz, 1H), 7.1 (t, J=7 Hz, 1H), 7. (dd, J=9 and 2 Hz, 1H), 6.83 (d, J=2 Hz, 1H), 5.82 (s, 2H), 3.86-3.88 (m, 2H), 3.86 (s, 3H), 2.68 (t, J=12 Hz, 2H), 1.75 (d, J=12 Hz, 2H), 1.4-1.5 (m, 1H), 1.32 (dq, J=12 Hz and 2.8 Hz, 2H), 1.2-1.24 (m, 1H), 0.9 (d, J=7 Hz, 6H). $^{13}C$ NMR, 100 MHz, (DMSO-$d_6$): δ ppm 156.6, 151.8, 147.9, 136.8, 135.5, 128.8, 127.6, 126.5, 121.7, 119.5, 119.3, 117, 114.3, 114.1, 110.4, 110.1, 107.2, 49.1, 32.6, 32, 28.6, 19.7. HRMS (ESI) Calcd for $C_{26}H_{31}N_4$[$MH^+$]: 399.2543. Found: 299.2541. Anal. Calcd for $C_{26}H_{30}N_4$: C, 78.35; H, 7.59. Found: C, 78.41; H, 7.70.

7-(4-Benzylpiperidin-1-yl)-3-(1-methyl-1H-indol-3-yl)quinolin-2-amine (ISQ-5)

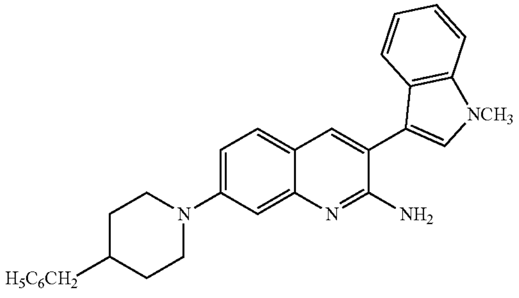

Purified by recrystallization from acetonitrile and dichloromethane: Yield 63%. $^1H$ NMR, 500 MHz (DMSO-$d_6$): δ ppm 7.76 (s, 1H), 7.58 (s, 1H), 7.49-7.55 (m, 3H), 7.3 (t, J=8.5 Hz, 2H), 7.18-7.25 (m, 4H), 7.1 (dt, J=8.5 Hz and 1 Hz, 1H), 6.99 (dd, J=9 Hz and 2.5 Hz, 1H), 6.82 (d, J=2 Hz, 1H), 5.82 (s, 2H), 3.86 (s, 3H), 3.81 (d, J=12 Hz, 2H), 2.69 (t, J=12.5 Hz, 2H), 2.56 (d, J=6.5 Hz, 2H), 1.67-1.75 (m, 3H), 1.33 (dq, J=12 Hz and 3 Hz, 2H). $^{13}C$ NMR, 100 MHz, (DMSO-$d_6$): δ ppm 156.5, 151.8, 147.7, 140.3, 136.8, 135.6, 129.1, 128.8, 128.2, 127.7, 126.5, 125.8, 121.7, 119.5, 119.3, 116.9, 114.3, 114.1, 110.3, 110.1, 107.1, 48.7, 42.3, 37.4, 32.6, 31.3. HRMS (ESI) Calcd for $C_{30}H_{31}N_4$[$MH^+$]: 447.2543. Found: 447.2544. Anal. Calcd for $C_{30}H_{30}N_4'2CH_3CN$: C, 79.71; H, 6.80. Found: C, 80.06; H, 6.71.

3-(1-Methyl-1H-indol-3-yl)-7-(4-phenylpiperidin-1-yl)quinolin-2-amine (ISQ-6)

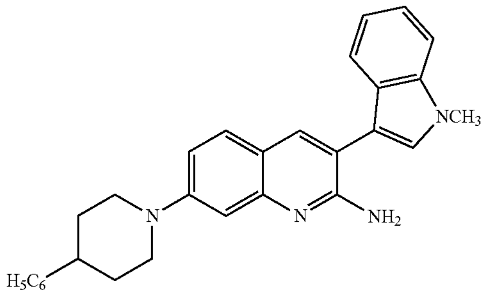

Purified by recrystallization from acetonitrile: Yield 42%. 1H NMR, 400 MHz (DMSO-$d_6$): δ ppm 7.8 (s, 1H), 7.6 (s, 1H), 7.52-7.56 (m, 3H), 7.18-7.34 (m, 6H), 7.11 (t, J=7.6 Hz, 1H), 7.07 (dd, J=9.2 Hz and 2.4 Hz, 1H), 6.9 (d, J=2 Hz, 1H), 5.92 (s, 2H), 3.97 (d, J=12.8 Hz, 2H), 386 (s, 3H), 2.88 (dt, J=12 Hz and 2.4 Hz, 2H), 2.75 (tt, J=12 Hz and 4 Hz, 1H), 1.89-1.92 (m, 2H), 1.81 (dt, J=12 Hz and 4 Hz, 2H). $^{13}C$ NMR, 100 MHz, (DMSO-$d_6$): δ ppm 156.6, 151.8, 146.1, 136.8, 135.6, 128.8, 128.4, 127.8, 126.7, 126.5, 126.1, 121.7, 119.5, 119.3, 117.1, 114.4, 114.2, 110.3, 110.2, 107.3, 49.2, 41.7, 32.6, 32.6. HRMS (ESI) Calcd for $C_{29}H_{29}N_4[MH^+]$: 433.2387. Found: 433.2390. Anal. Calcd for $C_{29}H_{28}N_4$ ½ $CH_3CN$: C, 79.53; H, 6.56. Found: C, 79.73; H, 6.55.

1-(2-Amino-3-(1-methyl-1H-indol-3-yl)quinolin-7-yl)piperidine-4-carbonitrile (ISQ-7)

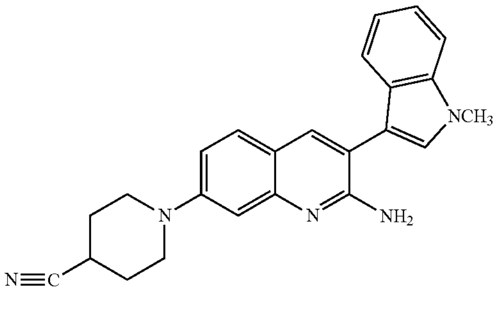 [SMILES: Cn1cc(-c2cc3ccc(N4CCC(C#N)CC4)cc3nc2N)c2ccccc21]

Purified by recrystallization from acetonitrile: Yield 39%. $^1H$ NMR, 500 MHz (DMSO-$d_6$): δ ppm 7.79 (s, 1H), 7.6 (s, 1H), 7.51-7.56 (m, 3H), 7.24 (t, J=7.5 Hz, 1H), 7.11 (t, J=7.5 Hz, 1H), 7.01 (dd, J=9 Hz and 2.5 Hz, 1H), 6.86 (d, J=2.5 Hz, 1H), 5.88 (s, 2H), 3.86 (s, 3H), 3.45-3.5 (m, 2H), 3.16 (ddd, J=12 Hz, 9 Hz and 4 Hz, 2H), 3.08 (septet, J=4 Hz, 1H), 2-2.04 (m, 2H), 1.82-1.89 (m, 2H). $^{13}C$ NMR, 100 MHz, (DMSO-$d_6$): δ ppm 156.8, 151.3, 148, 136.8, 135.4, 128.8, 127.8, 126.5, 122.3, 121.7, 119.5, 119.3, 117.4, 114.8, 114.1, 110.4, 110.1, 107.9, 47, 32.6, 27.8, 25.3. HRMS (ESI) Calcd for $C_{24}H_{24}N_5[MH^+]$: 382.2026. Found: 382.2034. Anal. Calcd for $C_{24}H_{23}N_5$: C, 75.56; H, 6.08. Found: C, 75.57; H, 6.05.

(1-(2-Amino-3-(1-methyl-1H-indol-3-yl)quinolin-7-yl)piperidin-4-yl)methanol (ISQ-8)

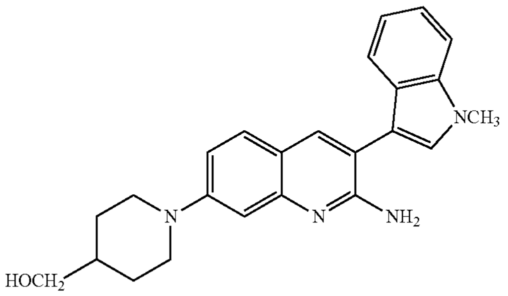

Purified by recrystallization from acetonitrile and dichloromethane: Yield 43%. $^1H$ NMR, 400 MHz (DMSO-$d_6$): δ ppm 7.77 (s, 1H), 7.58 (s, 1H), 7.49-7.56 (m, 3H), 7.23 (t, J=7.2 Hz, 1H), 7.11 (t, J=7.2 Hz, 1H), 7 (dd, J=8.8 Hz and 2.4 Hz, 1H), 6.84 (d, J=2.4 Hz, 1H), 5.85 (s, 2H), 4.52 (s, 1H), 3.85 (s, 3H), 3.81-3.85 (m, 2H), 3.31 (d, J=6.4 Hz, 2H), 2.74 (dt (J=12.4 Hz and 2.4 Hz, 2H), 1.77 (d, J=12.4 Hz, 2H), 1.53-1.61 (m, 1H), 1.26 (dq, J=12.4 Hz and 4 Hz, 2H). $^{13}C$ NMR, 100 MHz, (DMSO-$d_6$): δ ppm 156.7, 151.8, 148.1, 136.8, 135.5, 128.8, 127.6, 126.5, 121.7, 119.5, 119.3, 117, 114.3, 114.1, 110.5, 110.1, 107.4, 65.9, 48.6, 38.4, 28.3. HRMS (ESI) Calcd for $C_{24}H_{27}N_4O$ $[MH^+]$: 387.2179. Found: 387.2198. Anal. Calcd for $C_{24}H_{26}N_4O$ $2CH_3CN$: C, 71.77; H, 6.88. Found: C, 71.81; H, 6.60.

7-(4-(Methoxymethyl)piperidin-1-yl)-3-(1-methyl-1H-indol-3-yl)quinolin-2-amine (ISQ-9)

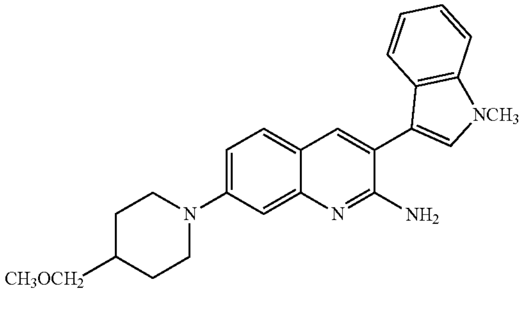

Purified by recrystallization from acetonitrile and dichloromethane: Yield 50%. $^1H$ NMR, 400 MHz (DMSO-$d_6$): δ ppm 7.78 (s, 1H), 7.59 (s, 1H), 7.49-7.56 (m, 3H), 7.24 (t, J=7.2 Hz, 1H), 7.11 (t, J=7.2 Hz, 1H), 7 (dd, J=9 Hz and 2.4 Hz, 1H), 6.85 (d, J=2.4 Hz, 1H), 5.92 (s, 2H), 3.85 (s, 3H), 3.82 (d, J=12.4 Hz, 2H), 3.25 (s, 3H), 3.21 (d, J=5.6 Hz, 2H), 2.75 (t, J=12.4 Hz, 2H), 1.7-1.76 (m, 3H), 1.3 (dq, J=12.4 Hz and 2.4 Hz, 2H). $^{13}C$ NMR, 100 MHz, (DMSO-$d_6$): δ ppm 156.6, 151.8, 147.8, 136.8, 135.6, 128.8, 127.7, 126.5, 121.7, 119.5, 119.3, 116.9, 114.3, 114.1, 110.3, 110.1, 107.2, 76.9, 58.2, 48.4, 35.7, 32.6, 28.3. HRMS (ESI) Calcd for $C_{25}H_{29}N_4O$ $[MH^+]$: 401.2336. Found: 401.2335.

3-(1-Methyl-1H-indol-3-yl)-7-(4-(pyridin-4-yl)piperidin-1-yl)quinolin-2-amine (ISQ-10)

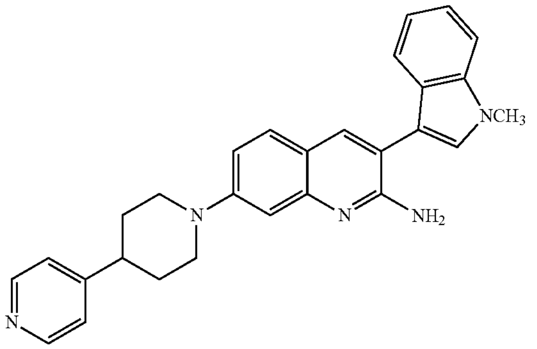 [SMILES: Cn1cc(-c2cc3ccc(N4CCC(c5ccncc5)CC4)cc3nc2N)c2ccccc21]

Purified by recrystallization from methanol and dichloromethane: Yield 68%. $^1$H NMR, 500 MHz ($CDCl_3$): δ ppm 8.53-8.54 (m, 2H), 7.81 (s, 1H), 7.64 (d, J=7.5 Hz, 1H), 7.53 (d, J=9 Hz, 1H), 7.42 (d, J=8 Hz, 1H), 7.32 (t, J=8 Hz, 1H), 7.27 (s, 1H), 7.18 (p, J=1.5 Hz, 3H), 7.13 (d, J=2 Hz, 1H), 7.07 (dd, J=9 Hz and 2 Hz, 1H), 4.98 (s, 2H), 4.03 (d, J=12.5 Hz, 2H), 3.89 (s, 3H), 2.97 (dt, J=12.5 Hz and 2.5 Hz, 2H), 2.7-2.75 (m, 1H), 1.9-2.01 (m, 4H). $^{13}$C NMR, 100 MHz, ($CDCl_3$): δ ppm 156.8, 154.7, 152.4, 150.1, 148.5, 137.3, 137.1, 128, 126.9, 122.5, 122.4, 120.2, 120.1, 118.4, 115.6, 115.1, 111.8, 109.8, 109, 50, 42.1, 33.1, 32.3. HRMS (ESI) Calcd for $C_{28}H_{28}N_5[MH^+]$: 434.2339. Found: 434.2338. Anal. Calcd for $C_{28}H_{27}N_5$ HCl: C, 71.55; H, 6.00. Found: C, 71.94; H, 5.97.

Biology

Materials.

Antibodies: Axin2 (#2151, Cell signaling technology), c-Myc (#1472-1, Epitomics), β-actin (#A1978, Sigma), pACC (#11818, Cell signaling technology), Total ACC (#3676, Cell signaling technology), pAMPK (#2535, Cell signaling technology), Total AMPK (#2532, Cell signaling technology), GAPDH (#GTX627408, GeneTex), Plk1 (#sc-17783, Santa Cruz), cyclinD1 (#2978, Cell signaling technology), cyclinB1 (#4135, Cell signaling technology), p-Akt (#9272, Cell signaling technology), Total-Akt (#1081-1, Epitomics), p-P70S6K (#9234, Cell signaling technology), Total-P70S6K (#2708, Cell signaling technology), p-4E-BP1 (#2855, Cell signaling technology), Total-4E-BP1 (#GTX109162, GeneTex), p-CDC2 (#9111, Cell signaling technology), Total-CDC2 (#GTX108120, GeneTex). Compounds: GSK461364 was purchased from Cayman Chemical (Ann Arbor, MI, USA). BI2536 was from Achemblock (Burlingame, CA). DAPI and PI were from ThermoFisher (Waltham, MA).

Cell Lines and Cell Culture

LS174T cell line (LS174T-TR4) is a gift from Professor Hans Clevers and Marc van de Wetering. LS174T-TR4 cells were selected with resistance to blasticidin (57). PC3 and Beas-2B cells are obtained from Professor Vivek Rangnekar and have been authenticated for previous publications (58). SK-LMS-1 and HepG2 cells were purchased from American Type Culture Collection (ATCC) in 2019. *Mycoplasma* testing were performed using a sensitive PCR-based *mycoplasma* detection kit covering more than 200 species/strains of mycoplasmas (Biovision, K1476-100), and no *mycoplasma* contamination was found in the cell lines used in this work. All cells were cultured in the media recommended by ATCC at 37° C. with 5% $CO_2$ atmosphere in a water jacketed incubator (NuAire, Plymouth, MN).

Western Blotting

Western blotting were performed according to previous procedures (25). Cells were split into 12-well plates. After 24 hours, compounds at indicated final concentrations were added to each well for another 24 hours unless otherwise noted. DMSO was used as a control. Cells were lysed in the appropriate volume of lysis buffer: 50 mM HEPES, 100 mM NaCl, 2 mM EDTA, 1% (v/v) glycerol, 50 mM NaF, 1 mM $Na_3VO_4$, 1% (v/v) Triton X-100, with protease inhibitors. Cell lysates were centrifuged, and supernatants were mixed with 6× protein loading buffer and boiled. The obtained samples were analyzed with standard western blotting methods with indicated antibodies.

Cell Proliferation Inhibition Assay

Cell proliferation inhibition assays were done following a previous report (32). Cancer cells were seeded into 24-well plates at a density of 20,000 cells per well in 1 mL of culture medium and were cultured overnight at 37° C. Compounds and the vehicle control (DMSO) were added to the cells. After 5 days, the medium was removed, and 100 μL of trypsin was added. The cells were resuspended in phosphate-buffered saline (PBS) and were counted by Vi-CELL XR 2.03 (Beckman Coulter, Inc. USA). The ratio R of the number of viable cells in the compound treatment group to the number of viable cells in DMSO treatment group was taken as relative growth, and the percentage growth inhibition was calculated as (1−R)*100.

Reporter Assay

Wnt reporter assay was described previously (25). We subcloned Super 8×TOPFlash (provided by Professor Randall Moon, University of Washington) into the pGL4.83 [hRlucP/Puro] Vector and transfected it into HEK293T cells. A stable HEK293T cell line containing the TOPFlash reporter was established using puromycin selection (25). To assess if compounds of interest blocked the downstream signaling transduction pathway of β-catenin, the stable reporter cells were seeded to a 12-well plate and treated with 25 mM LiCl to stabilize β-catenin for 16 hours to activate Wnt signaling and then candidate compounds at predetermined concentrations for another 24 hours. The cells were lysed and centrifuged to obtain supernatants which were analyzed by FB 12 Single Tube Luminometer by Titertek-Berthold (Berthold Detection Systems GmbH, Elsässerstr, Germany).

Seahorse Assay

Seahorse assays were carried out following a published procedure (25). Briefly, 2.5×10$^4$ cells in 80 μL of medium were seeded in XF96 Cell Culture microplate for all experiments. On the next day, cell culture media were replaced with Seahorse XF modified media. Cells were treated with 1 μM of oligomycin A, 1.0 μM FCCP and mixture of 1.0 μM of rotenone and 1.0 μM of antimycin A in standard mitochondrial stress test conditions. To determine the uncoupler effects, FCCP was replaced with an equal volume of DMSO, or a compound to be tested in DMSO solution. To test whether compounds inhibited ETC complex V, oligomycin was replaced with an equal volume of DMSO, or compounds in DMSO solution. To assess if compounds inhibited ETC complex I or III, rotenone and antimycin A were replaced with an equal volume of DMSO, or compounds in DMSO solution.

Mitochondrial ETC Complex Activity Measurements Using PMP

Mitochondrial ETC complex activity measurements were taken using the Agilent Seahorse Assay with XF PMP (Agilent, Santa Clara, CA) following manufacturer's instructions. Adherent monolayer cells were gently washed with mitochondrial assay solution (MAS) (220 mM mannitol, 70 mM sucrose, 10 mM $KH_2PO_4$, 5 mM $MgCl_2$, 2 mM HEPES, 1 mM EGTA, and 0.2% (w/v) fatty acid free BSA) and cell growth media was replaced with MAS supplemented with 4 mM adenosine diphosphate (ADP), 10 mM pyruvate, and 1 nM PMP. Following calibration, the assay was immediately performed by measuring baseline with two cycles of 0.5 min mixing, 0.5 min waiting, and 2 min measuring. After baseline measurements, sequential injections of DMSO, compounds of interest or 2 μM rotenone, 10 mM succinate, 2 μM antimycin A, and a combination of 10 mM ascorbate and 100 μM TMPD were also performed with each followed by two cycles of 0.5 min mixing, 0.5 min waiting, and 2 min measuring. Data were then normalized to cell counts using the Biotek Cytation 1 (BioTek Instruments, Winooski, VT, USA).

Calculation of Synergy Scores of ISQ-1 and BI2536

Cell proliferation inhibition assays described above were carried out using LS174T cells to evaluate the inhibitory effects of ISQ-1 with or without B12536 at predetermined concentrations. The final treatment concentrations of ISQ-1 were 0 nM, 50 nM, 100 nM, 200 nM, 300 nM, and 400 nM in the presence or absence of B12536 at 0 nM, 1 nM, 1.5 nM, 3 nM, 4.5 nM and 6 nM. Synergy scores were calculated using SynergyFinder web application (Version 2.0) at default parameters with Bliss as the reference model (37).

Cell Cycle Analysis by Flow Cytometry

Cell cycle analysis by flow cytometry was done following a previous report (32). Briefly, a million of LS174T cells were placed in 6-cm dishes and cultured at 37° C. for 24 hours. DMSO or compounds in DMSO were added to the cells and incubated for additional 24 hours. The cells were trypsinized, washed with ice cold PBS twice, and resuspended in 500 μL of PBS. This cell suspension was added to 5 mL of 70% ethanol dropwise in a 15 mL tube that was placed on vortex and kept at −20° C. overnight. The cells were further washed with PBS and 2 μL of 50 mg/ml RNase (final 0.2 mg/ml) and 2.5 μL of 4 mg/mL PI (final 20 μg/mL) were added. The mixture was incubated at dark for 45 min and filtered through 35 μm nylon mesh for analysis by the Flow Cytometry and Cell Sorting Shared Resource Facility of the University of Kentucky Markey Cancer Center.

Colon Cancer Organoids

The colon cancer organoids were isolated from $Apc^{fl/+}$/$Kras^{LSL-G12D}$/Villin-Cre mouse model (38). Using 48-well drug screening to assess how compounds affected organoid colony formation, the Matrigel containing organoids was digested by 300 μL dispase. The gel was removed by 1,000×5 min spinning. The organoids were digested into single cells by 1 mL Trypsin and washed with 10 mL of ADF12. For each well, 80 μL of Matrigel was added to the bottom and 1000 cells in 60 μL Matrigel were added to the top. The cells were cultured in 250 μL of 3D complete medium (Advanced DMEM/F12 supplemented with 1×N-2, 1×B-27, 1 mM N-acetylcysteine and 1% penicillin/streptomycin). The cells were treated with DMSO or testing compounds and total number of organoids with diameter greater than 50 μm were analyzed and manually counted using microscope.

To evaluate whether compounds inhibited organoid growth, above procedures were followed and 10,000 single cells/per well were plated in 24-well plate. After 3 days when organoids formed, fresh culture media were supplied, and compounds were added for additional 3 days. Organoid viability was measured using CellTiter-Glo® 3D Cell Viability Assay (Promega) following manufacturer's protocol.

In Vivo Evaluation of Antineoplastic Activity and Gross Toxicity in LS174T Xenografts Mouse studies were carried out with approval from the Institutional Animal Care and Use Committee of the University of Kentucky (2020-3531). All methods were performed in accordance with the relevant guidelines and regulations according to protocols. LS174T cells suspended in 50% Matrigel (Corning, Glendale, Arizona) were subcutaneously injected in the lower flanks of severe combined immunodeficient mice (12 male mice and 8 female mice) at a density of $1\times10^6$ cells in 100 L of 50% Matrigel. After tumors were established, mice were randomized according to tumor volume and divided into groups for treatments (five mice in each group, two tumors on each mouse).

The in vivo evaluation of ISQ-1 and BI2536 followed the approved protocol. After tumors were established, ISQ-1 was formulated in a mixture of Tween-80 (5%), DMSO (10%), PEG400 (25%) and PBS (60%) and was intraperitoneally administered to the ISQ-1 group at a daily dose of 20 mg/kg mouse body weight. The first day of treatment was set as day 0. At days 0, 4, and 7, BI2536 dissolved in 0.1 N HCl and then diluted 5-fold using 0.9% NaCl was given via gavage to the B12536 group. Mice in combination therapy group were treated with both ISQ-1 and BI2536 following aforementioned dosing schedules. At day 11 treatment was ceased and mice were sacrificed. Tumors and mouse weights were measured, and tumor volumes were calculated as Length×width$^2$/2.

Statistics

Major biological assays were performed at least twice. Data were shown as mean SEM. For the mice study, five mice with two tumors on the lower flanks of each mouse were used in each treatment group. Sizes of the two tumors from each mouse were averaged, standardized by the tumor size on day 0, and log-transformed. ANOVA with Tukey's HSD test was used to compare the tumor size at the end of the study (day 11) between the combination therapy of ISQ-1 and B12536 and each single compound as well as the control. The equal variance assumption of ANOVA was assessed by Bartlett's test. All statistical studies were overseen in collaboration with a statistician in the University of Kentucky's Markey Cancer Center.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Ashton T M, McKenna W G, Kunz-Schughart L A, Higgins G S. Oxidative Phosphorylation as an Emerging Target in Cancer Therapy. Clin Cancer Res 2018; 24(11): 2482-90 doi 10.1158/1078-0432.CCR-17-3070.
2. Weinberg S E, Chandel N S. Targeting mitochondria metabolism for cancer therapy. Nat Chem Biol 2015; 11(1):9-15 doi 10.1038/nchembio.1712.
3. Chandel N S. Mitochondria as signaling organelles. BMC Biol 2014; 12:34 doi 10.1186/1741-7007-12-34.
4. DeBerardinis R J, Chandel N S. Fundamentals of cancer metabolism. Science advances 2016; 2(5):e1600200 doi 10.1126/sciadv.1600200.

5. Vyas S, Zaganjor E, Haigis M C. Mitochondria and Cancer. Cell 2016; 166(3):555-66 doi 10.1016/j.cell.2016.07.002.
6. Wolf D A. Is reliance on mitochondrial respiration a "chink in the armor" of therapy-resistant cancer? Cancer cell 2014; 26(6):788-95 doi 10.1016/j.ccell.2014.10.001.
7. Zhang G, Frederick D T, Wu L, Wei Z, Krepler C, Srinivasan S, et al. Targeting mitochondrial biogenesis to overcome drug resistance to MAPK inhibitors. J Clin Invest 2016; 126(5):1834-56 doi 10.1172/JCI82661.
8. Roesch A, Vultur A, Bogeski I, Wang H, Zimmermann K M, Speicher D, et al. Overcoming intrinsic multidrug resistance in melanoma by blocking the mitochondrial respiratory chain of slow-cycling JARID1B(high) cells. Cancer cell 2013; 23(6):811-25 doi 10.1016/j.ccr.2013.05.003.
9. Zu X L, Guppy M. Cancer metabolism: facts, fantasy, and fiction. Biochem Biophys Res Commun 2004; 313(3): 459-65 doi 10.1016/j.bbrc.2003.11.136.
10. Larman T C, DePalma S R, Hadjipanayis A G, Cancer Genome Atlas Research N, Protopopov A, Zhang J, et al. Spectrum of somatic mitochondrial mutations in five cancers. Proc Natl Acad Sci USA 2012; 109(35):14087-91 doi 10.1073/pnas.1211502109.
11. Yu M. Generation, function and diagnostic value of mitochondrial DNA copy number alterations in human cancers. Life Sci 2011; 89(3-4):65-71 doi 10.1016/j.lfs.2011.05.010.
12. Birsoy K, Possemato R, Lorbeer F K, Bayraktar E C, Thiru P, Yucel B, et al. Metabolic determinants of cancer cell sensitivity to glucose limitation and biguanides. Nature 2014; 508(7494):108-12 doi 10.1038/nature13110.
13. Dang C V. MYC on the path to cancer. Cell 2012; 149(1):22-35 doi 10.1016/j.cell.2012.03.003.
14. Kalkat M, De Melo J, Hickman K A, Lourenco C, Redel C, Resetca D, et al. MYC Deregulation in Primary Human Cancers. Genes (Basel) 2017; 8(6) doi 10.3390/genes8060151.
15. Carabet L A, Rennie P S, Cherkasov A. Therapeutic Inhibition of Myc in Cancer. Structural Bases and Computer-Aided Drug Discovery Approaches. Int J Mol Sci 2018; 20(1) doi 10.3390/ijms20010120.
16. Dang C V. MYC, metabolism, cell growth, and tumorigenesis. Cold Spring Harb Perspect Med 2013; 3(8) doi 10.1101/cshperspect.a014217.
17. Nesbit C E, Tersak J M, Prochownik E V. MYC oncogenes and human neoplastic disease. Oncogene 1999; 18(19):3004-16 doi 10.1038/sj.onc.1202746.
18. Secombe J, Pierce S B, Eisenman R N. Myc: a weapon of mass destruction. Cell 2004; 117(2):153-6 doi 10.1016/s0092-8674(04)00336-8.
19. Shi L, Wu Y X, Yu J H, Chen X, Luo X J, Yin Y R. Research of the relationship between beta-catenin and c-myc-mediated Wnt pathway and laterally spreading tumors occurrence. Eur Rev Med Pharmacol Sci 2017; 21(2):252-7.
20. Jain M, Arvanitis C, Chu K, Dewey W, Leonhardt E, Trinh M, et al. Sustained loss of a neoplastic phenotype by brief inactivation of MYC. Science 2002; 297(5578): 102-4 doi 10.1126/science.1071489.
21. Soucek L, Whitfield J, Martins C P, Finch A J, Murphy D J, Sodir N M, et al. Modelling Myc inhibition as a cancer therapy. Nature 2008; 455(7213):679-83 doi 10.1038/nature07260.
22. Horiuchi D, Anderton B, Goga A. Taking on challenging targets: making MYC druggable. Am Soc Clin Oncol Educ Book 2014:e497-502 doi 10.14694/EdBook_AM.2014.34.e497.
23. Wolf E, Eilers M. Targeting MYC Proteins for Tumor Therapy. Annual Review of Cancer Biology 2020; 4(1): 61-75 doi 10.1146/annurev-cancerbio-030518-055826.
24. Chen H, Liu H, Qing G. Targeting oncogenic Myc as a strategy for cancer treatment. Signal Transduct Target Ther 2018; 3:5 doi 10.1038/s41392-018-0008-7.
25. Zhang W, Sviripa V M, Kril L M, Yu T, Xie Y, Hubbard W B, et al. An Underlying Mechanism of Dual Wnt Inhibition and AMPK Activation: Mitochondrial Uncouplers Masquerading as Wnt Inhibitors. J Med Chem 2019; 62(24):11348-58 doi 10.1021/acs.jmedchem.9b01685.
26. Akinyeke T, Matsumura S, Wang X, Wu Y, Schalfer E D, Saxena A, et al. Metformin targets c-MYC oncogene to prevent prostate cancer. Carcinogenesis 2013; 34(12): 2823-32 doi 10.1093/carcin/bgt307.
27. Welcker M, Orian A, Jin J, Grim J E, Harper J W, Eisenman R N, et al. The Fbw7 tumor suppressor regulates glycogen synthase kinase 3 phosphorylation-dependent c-Myc protein degradation. Proc Natl Acad Sci USA 2004; 101(24):9085-90 doi 10.1073/pnas.0402770101.
28. Tan J, Li Z, Lee P L, Guan P, Aau M Y, Lee S T, et al. PDK1 signaling toward PLK1-MYC activation confers oncogenic transformation, tumor-initiating cell activation, and resistance to mTOR-targeted therapy. Cancer Discov 2013; 3(10):1156-71 doi 10.1158/2159-8290.CD-12-0595.
29. Gutteridge R E, Ndiaye M A, Liu X, Ahmad N. Plk1 Inhibitors in Cancer Therapy: From Laboratory to Clinics. Mol Cancer Ther 2016; 15(7):1427-35 doi 10.1158/1535-7163.MCT-15-0897.
30. Burikhanov R, Sviripa V M, Hebbar N, Zhang W, Layton W J, Hamza A, et al. Arylquins target vimentin to trigger Par-4 secretion for tumor cell apoptosis. Nat Chem Biol 2014; 10(11):924-6 doi 10.1038/nchembio.1631.
31. Frasinyuk M S, Zhang W, Wyrebek P, Yu T, Xu X, Sviripa V M, et al. Developing antineoplastic agents that target peroxisomal enzymes: cytisine-linked isoflavonoids as inhibitors of hydroxysteroid 17-beta-dehydrogenase-4 (HSD17B4). Org Biomol Chem 2017; 15(36): 7623-9 doi 10.1039/c7ob01584d.
32. Xie Y, Kril L M, Yu T, Zhang W, Frasinyuk M S, Bondarenko S P, et al. Semisynthetic aurones inhibit tubulin polymerization at the colchicine-binding site and repress PC-3 tumor xenografts in nude mice and myc-induced T-ALL in zebrafish. Sci Rep 2019; 9(1):6439 doi 10.1038/s41598-019-42917-0.
33. Zhang W, Sviripa V, Chen X, Shi J, Yu T, Hamza A, et al. Fluorinated N,N-dialkylaminostilbenes repress colon cancer by targeting methionine S-adenosyltransferase 2A. ACS Chem Biol 2013; 8(4):796-803 doi 10.1021/cb3005353.
34. Zhang W, Sviripa V, Kril L M, Chen X, Yu T, Shi J, et al. Fluorinated N,N-dialkylaminostilbenes for Wnt pathway inhibition and colon cancer repression. J Med Chem 2011; 54(5):1288-97 doi 10.1021/jm101248v.
35. Salabei J K, Gibb A A, Hill B G. Comprehensive measurement of respiratory activity in permeabilized cells using extracellular flux analysis. Nat Protoc 2014; 9(2): 421-38 doi 10.1038/nprot.2014.018.
36. Divakaruni A S, Wiley S E, Rogers G W, Andreyev A Y, Petrosyan S, Loviscach M, et al. Thiazolidinediones are acute, specific inhibitors of the mitochondrial pyruvate carrier. Proc Natl Acad Sci USA 2013; 110(14):5422-7 doi 10.1073/pnas.1303360110.
37. Ianevski A, Gir A K, Aittokallio T. SynergyFinder 2.0: visual analytics of multi-drug combination synergies. Nucleic Acids Res 2020; 48(W1):W488-W93 doi 10.1093/nar/gkaa216.
38. Wen Y A, Xing X, Harris J W, Zaytseva Y Y, Mitov M I, Napier D L, et al. Adipocytes activate mitochondrial fatty acid oxidation and autophagy to promote tumor growth in colon cancer. Cell Death Dis 2017; 8(2):e2593 doi 10.1038/cddis.2017.21.
39. Xiong X, Wen Y A, Fairchild R, Zaytseva Y Y, Weiss H L, Evers B M, et al. Upregulation of CPT1A is essential for the tumor-promoting effect of adipocytes in colon cancer. Cell Death Dis 2020; 11(9):736 doi 10.1038/s41419-020-02936-6.
40. Kril L M, Vilchez V, Jiang J, Turcios L, Chen C, Sviripa V M, et al. N-Aryl benzenesulfonamide inhibitors of [3H]-thymidine incorporation and beta-catenin signaling in human hepatocyte-derived Huh-7 carcinoma cells. Bioorg Med Chem Lett 2015; 25(18):3897-9 doi 10.1016/j.bmcl.2015.07.040.
41. Zhang W, Sviripa V, Xie Y, Yu T, Haney M, Blackburn J, et al. Epigenetic Regulation of Wnt Signaling by Carboxamide-substituted Benzhydryl Amines That Function as Histone Demethylase Inhibitors. iScience 2020; 101795.
42. Caro P, Kishan A U, Norberg E, Stanley I A, Chapuy B, Ficarro S B, et al. Metabolic signatures uncover distinct targets in molecular subsets of diffuse large B cell lymphoma. Cancer cell 2012; 22(4):547-60 doi 10.1016/j.ccr.2012.08.014.
43. Vazquez F, Lim J H, Chim H, Bhalla K, Gimun G, Pierce K, et al. PGC1alpha expression defines a subset of human melanoma tumors with increased mitochondrial capacity and resistance to oxidative stress. Cancer cell 2013; 23(3):287-301 doi 10.1016/j.ccr.2012.11.020.
44. Lee K M, Giltnane J M, Balko J M, Schwarz L J, Guerrero-Zotano A L, Hutchinson K E, et al. MYC and MCL1 Cooperatively Promote Chemotherapy-Resistant Breast Cancer Stem Cells via Regulation of Mitochondrial Oxidative Phosphorylation. Cell Metab 2017; 26(4):633-47 e7 doi 10.1016/j.cmet.2017.09.009.
45. Lissanu Deribe Y, Sun Y, Terranova C, Khan F, Martinez-Ledesma J, Gay J, et al. Mutations in the SWI/SNF complex induce a targetable dependence on oxidative phosphorylation in lung cancer. Nat Med 2018; 24(7):1047-57 doi 10.1038/s41591-018-0019-5.
46. Molina J R, Sun Y, Protopopova M, Gera S, Bandi M, Bristow C, et al. An inhibitor of oxidative phosphorylation exploits cancer vulnerability. Nat Med 2018; 24(7):1036-46 doi 10.1038/s41591-018-0052-4.
47. Corazao-Rozas P, Guerreschi P, Jendoubi M, Andre F, Jonneaux A, Scalbert C, et al. Mitochondrial oxidative stress is the Achille's heel of melanoma cells resistant to Braf-mutant inhibitor. Oncotarget 2013; 4(11):1986-98 doi 10.18632/oncotarget.1420.
48. Haq R, Shoag J, Andreu-Perez P, Yokoyama S, Edelman H, Rowe G C, et al. Oncogenic BRAF regulates oxidative metabolism via PGClalpha and MITF. Cancer cell 2013; 23(3):302-15 doi 10.1016/j.ccr.2013.02.003.
49. Takenaka T, Katayama M, Sugiyama A, Hagiwara M, Fujii I, Takatani-Nakase T, et al. Gefitinib Enhances Mitochondrial Biological Functions in NSCLCs with EGFR Mutations at a High Cell Density. Anticancer Res 2017; 37(9):4779-88 doi 10.21873/anticanres.11884.
50. Gjertsen B T, Schoffski P. Discovery and development of the Polo-like kinase inhibitor volasertib in cancer therapy. Leukemia 2015; 29(1):11-9 doi 10.1038/leu.2014.222.
51. Xiao D, Yue M, Su H, Ren P, Jiang J, Li F, et al. Polo-like Kinase-1 Regulates Myc Stabilization and Activates a Feedforward Circuit Promoting Tumor Cell Survival. Mol Cell 2016; 64(3):493-506 doi 10.1016/j.molcel.2016.09.016.
52. Yuan J, Eckerdt F, Bereiter-Hahn J, Kurunci-Csacsko E, Kaufmann M, Strebhardt K. Cooperative phosphorylation including the activity of polo-like kinase 1 regulates the subcellular localization of cyclin B1. Oncogene 2002; 21(54):8282-92 doi 10.1038/sj.onc.1206011.
53. Schoffski P, Blay J Y, De Greve J, Brain E, Machiels J P, Soria J C, et al. Multicentric parallel phase II trial of the polo-like kinase 1 inhibitor BI 2536 in patients with advanced head and neck cancer, breast cancer, ovarian cancer, soft tissue sarcoma and melanoma. The first protocol of the European Organization for Research and Treatment of Cancer (EORTC) Network Of Core Institutes (NOCI). Eur J Cancer 2010; 46(12):2206-15 doi 10.1016/j.ejca.2010.03.039.
54. Casey S C, Tong L, Li Y, Do R, Walz S, Fitzgerald K N, et al. MYC regulates the antitumor immune response through CD47 and PD-L1. Science 2016; 352(6282):227-31 doi 10.1126/science.aac9935.
55. Kortlever R M, Sodir N M, Wilson C H, Burkhart D L, Pellegrinet L, Brown Swigart L, et al. Myc Cooperates with Ras by Programming Inflammation and Immune Suppression. Cell 2017; 171(6):1301-15 e14 doi 10.1016/j.cell.2017.11.013.
56. Han H, Jain A D, Truica M I, Izquierdo-Ferrer J, Anker J F, Lysy B, et al. Small-Molecule MYC Inhibitors Suppress Tumor Growth and Enhance Immunotherapy. Cancer cell 2019; 36(5):483-97 e15 doi 10.1016/j.ccell.2019.10.001.
57. Barker N, Hurlstone A, Musisi H, Miles A, Bienz M, Clevers H. The chromatin remodelling factor Brg-1 interacts with beta-catenin to promote target gene activation. EMBO J 2001; 20(17):4935-43 doi 10.1093/emboj/20.17.4935.
58. Hebbar N, Burikhanov R, Shukla N, Qiu S, Zhao Y, Elenitoba-Johnson K S J, et al. A Naturally Generated Decoy of the Prostate Apoptosis Response-4 Protein Overcomes Therapy Resistance in Tumors. Cancer Res 2017; 77(15):4039-50 doi 10.1158/0008-5472.CAN-16-1970.

It will be understood that various details of the presently disclosed subject matter can be changed without departing from the scope of the subject matter disclosed herein. Furthermore, the foregoing description is for the purpose of illustration only, and not for the purpose of limitation. Obvious modifications and variations are possible in light of the above teachings. All such modifications and variations are within the scope of the appended claims when interpreted in accordance with the breadth to which they are fairly, legally and equitably entitled.

What is claimed is:

1. An indole-substituted quinoline (ISQ) comprising a compound having a structure according to Formula I:

I

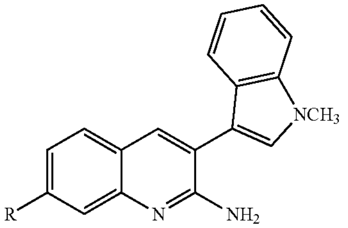

wherein R includes N $(R^1)_2$ or a substituted or unsubstituted six membered heterocycle including at least one nitrogen; and wherein $R^1$ includes an alkyl.

2. The compound of claim 1, having a substituted piperidine including a structure according to Formula II:

II

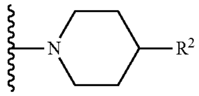

wherein $R^2$ includes branched or unbranched alkyl, hydroxyalkyl, alkoxyalkyl, cyano, aryl, arylalkyl, heteroaryl, or a combination thereof.

3. The compound of claim 1, having a substituted piperidine including a structure according to Formula III:

III

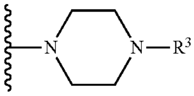

wherein $R^3$ includes a branched or unbranched alkyl.

4. The compound of claim 1, wherein the compound includes:

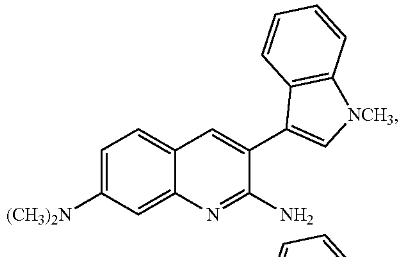

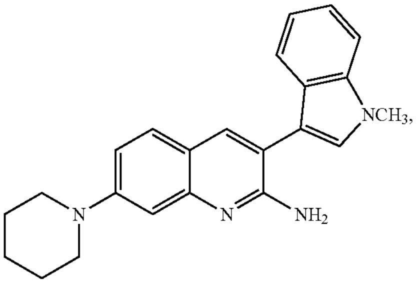

-continued

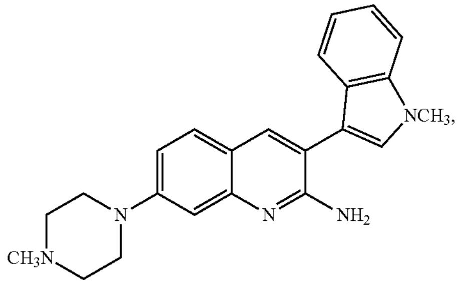

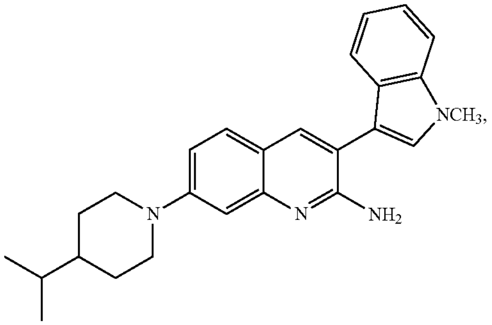

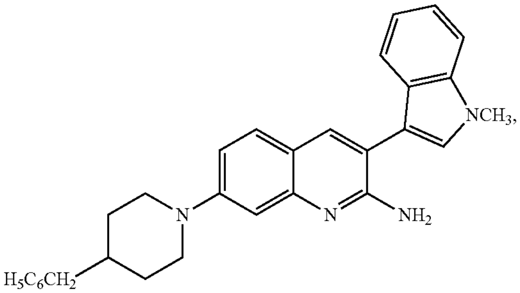

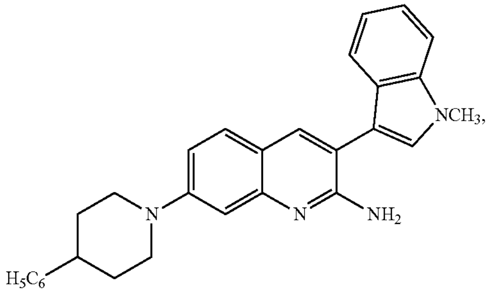

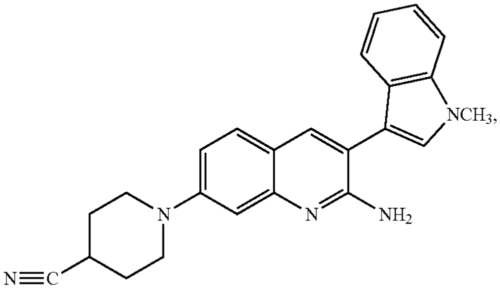

-continued

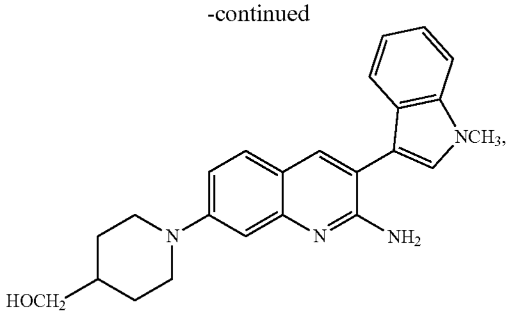

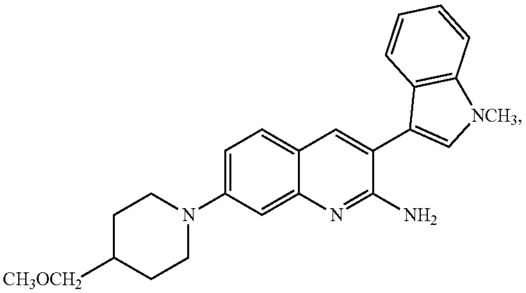

or

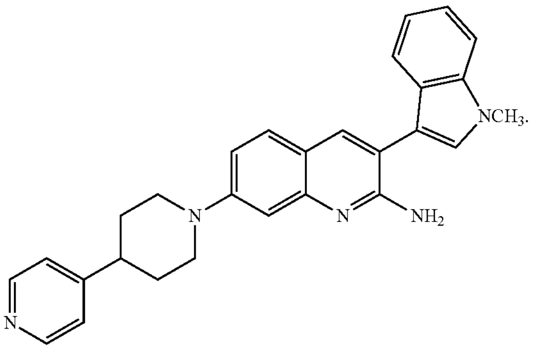

5. A method of treating cancer, the method comprising administering the compound according to claim 1 to a subject in need thereof.

6. The method of claim 5, further comprising administering a polo-like kinase-1 (Plk1) inhibitor with the compound according to claim 1.

7. The method of claim 6, further comprising administering the Plk1 inhibitor and the compound in synergistically effective amounts.

8. The method of claim 6, further comprising selecting the Plk1 inhibitor from the group consisting of BI2536, BI6727 (volasertib), GSK461364, NMS-1286937 (onvansertib), and combinations.

9. The method of claim 5, wherein the cancer is a c-MYC-driven cancer.

10. The method of claim 9, including selecting the cancer from the group consisting of: breast cancer, lymphoma, melanoma, lung cancer, colorectal cancer, neural cancer, ovarian cancer, prostate cancer, and combinations.

11. A method of treating cancer, the method comprising administering one or more of the compounds according to claim 4 to a subject in need thereof.

12. The method of claim 11, further comprising administering the Plk1 inhibitor and the one or more compounds in synergistically effective amounts.

13. The method of claim 11, further comprising selecting the Plk1 inhibitor from the group consisting of BI2536, BI6727 (volasertib), GSK461364, NMS-1286937 (onvansertib), and combinations.

14. The method of claim 11, wherein the cancer is a c-MYC-driven cancer.

15. The method of claim 14, including selecting the cancer from the group consisting of: breast cancer, lymphoma, melanoma, lung cancer, colorectal cancer, neural cancer, ovarian cancer, prostate cancer, and combinations.

16. A combination therapeutic, comprising:

an indole-substituted quinoline (ISQ) comprising a compound having a structure according to Formula I:

I

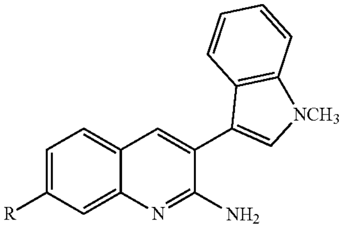

wherein R includes N $(R^1)_2$ or a substituted or unsubstituted six membered heterocycle including at least one nitrogen and wherein $R^1$ includes an alkyl; and a polo-like kinase-1 (Plk1) inhibitor.

17. The combination therapeutic of claim 16, having a substituted piperidine including a structure according to Formula II:

II

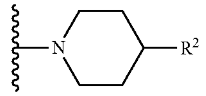

wherein $R^2$ includes branched or unbranched alkyl, hydroxyalkyl, alkoxyalkyl, cyano, aryl, arylalkyl, heteroaryl, or a combination thereof.

18. The combination therapeutic of claim 16, having a substituted piperidine including a structure according to Formula III:

III

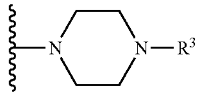

wherein $R^3$ includes a branched or unbranched alkyl.

19. The combination therapeutic of claim 16, wherein the compound includes:

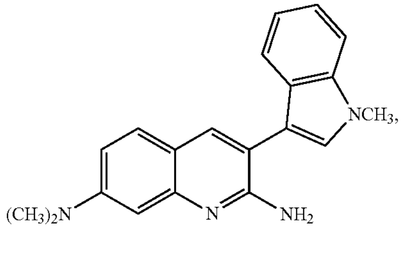

-continued

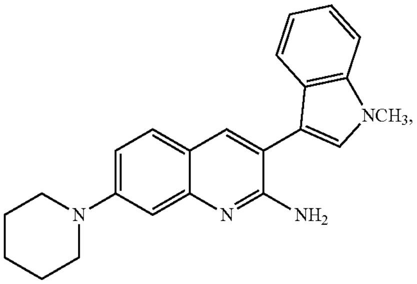

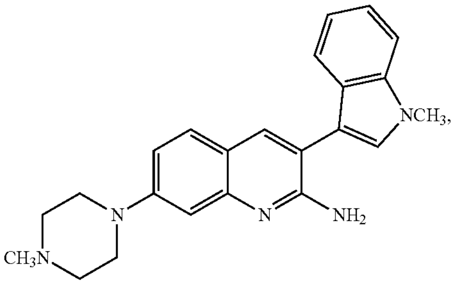

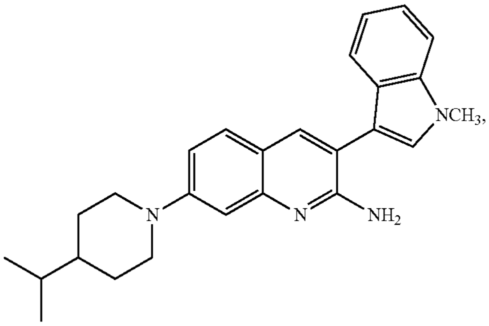

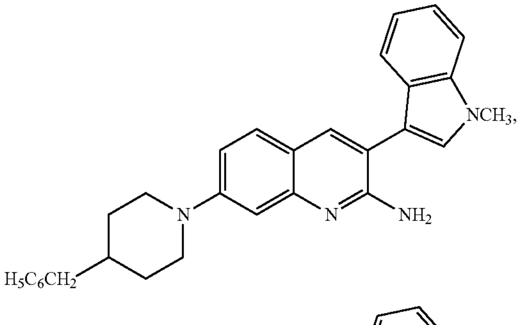

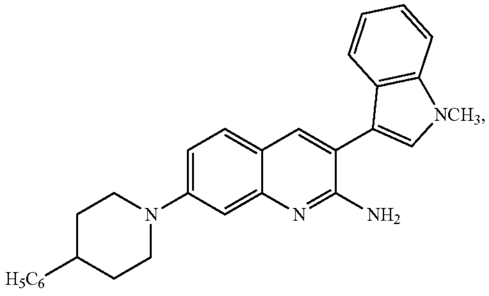

-continued

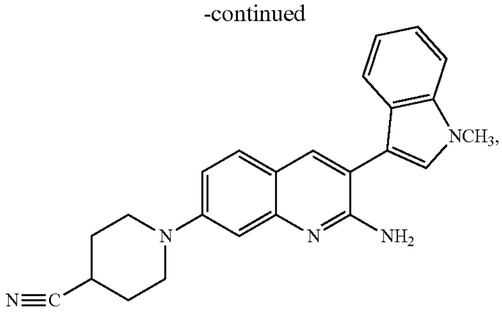

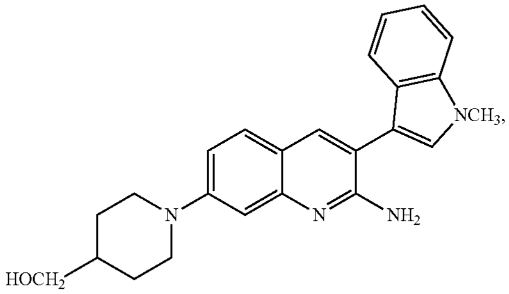

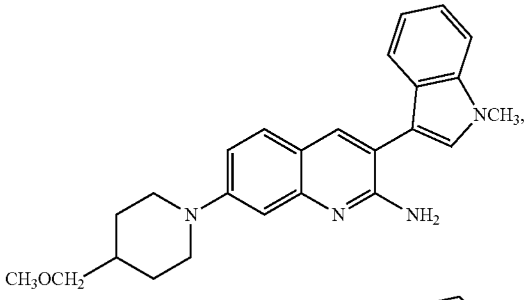

or

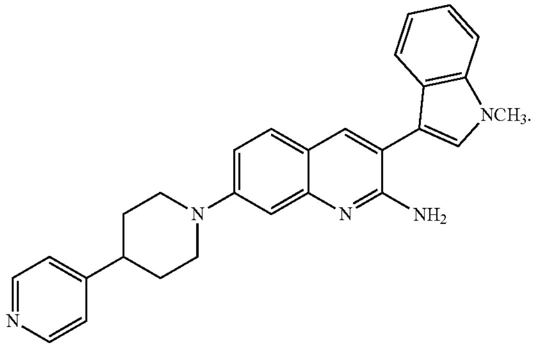

20. The combination therapeutic of claim 16, wherein the Plk1 inhibitor is selected from the group consisting of BI2536, BI6727 (volasertib), GSK461364, NMS-1286937 (onvansertib), and combinations.

21. The combination therapeutic of claim 16, wherein the Plk1 inhibitor and the compound are administered in synergistically effective amounts.

22. The combination therapeutic of claim 16, formulated for treating a cancer.

23. The combination therapeutic of claim 22, wherein the cancer is a c-MYC-driven cancer.

24. The combination therapeutic of claim 23, wherein the cancer is selected from the group consisting of: breast cancer, lymphoma, melanoma, lung cancer, colorectal cancer, neural cancer, ovarian cancer, prostate cancer, and combinations.

25. The combination therapeutic of claim 16, wherein the Plk1 inhibitor and the compound are administered in synergistically effective amounts.

26. The combination therapeutic of claim 19, formulated for treating a cancer.

27. The combination therapeutic of claim 26, wherein the cancer is a c-MYC-driven cancer.

28. The combination therapeutic of claim 27, wherein the cancer is selected from the group consisting of: breast cancer, lymphoma, melanoma, lung cancer, colorectal cancer, neural cancer, ovarian cancer, prostate cancer, and combinations.

* * * * *